US012070182B2

(12) United States Patent
Kakidani

(10) Patent No.: US 12,070,182 B2
(45) Date of Patent: Aug. 27, 2024

(54) SIGNAL PROCESSING DEVICE, IMAGING DEVICE, AND SIGNAL PROCESSING METHOD

(71) Applicant: SONY GROUP CORPORATION, Tokyo (JP)

(72) Inventor: Kei Kakidani, Tokyo (JP)

(73) Assignee: SONY GROUP CORPORATION, Tokyo (JP)

(*) Notice: Subject to any disclaimer, the term of this patent is extended or adjusted under 35 U.S.C. 154(b) by 339 days.

(21) Appl. No.: 17/593,505

(22) PCT Filed: Feb. 25, 2020

(86) PCT No.: PCT/JP2020/007431
§ 371 (c)(1),
(2) Date: Sep. 20, 2021

(87) PCT Pub. No.: WO2020/202904
PCT Pub. Date: Oct. 8, 2020

(65) Prior Publication Data
US 2022/0217260 A1 Jul. 7, 2022

(30) Foreign Application Priority Data
Mar. 29, 2019 (JP) ................. 2019-066240

(51) Int. Cl.
*H04N 23/667* (2023.01)
*A61B 1/00* (2006.01)
(Continued)

(52) U.S. Cl.
CPC .... *A61B 1/00006* (2013.01); *A61B 1/000095* (2022.02); *A61B 1/0661* (2013.01); *H04N 23/71* (2023.01); *H04N 23/73* (2023.01)

(58) Field of Classification Search
CPC .......... A61B 1/00006; A61B 1/000095; A61B 1/0661; A61B 1/00149; A61B 1/00188;
(Continued)

(56) References Cited

U.S. PATENT DOCUMENTS

| 2003/0142221 A1* | 7/2003 | Takakuwa | ............... H04N 23/60 348/222.1 |
| 2006/0077283 A1* | 4/2006 | Sasazaki | ................ H04N 9/315 348/E9.027 |

(Continued)

FOREIGN PATENT DOCUMENTS

| CN | 106027914 A | 10/2016 |
| CN | 106257917 A | 12/2016 |

(Continued)

OTHER PUBLICATIONS

International Search Report and Written Opinion of PCT Application No. PCT/JP2020/007431, issued on Apr. 21, 2020, 10 pages of ISRWO.

*Primary Examiner* — Van D Huynh
(74) *Attorney, Agent, or Firm* — CHIP LAW GROUP

(57) ABSTRACT

Mitigation of a discomfort of a user during brightness adjustment switching and curbing of deterioration in operability with respect to brightness adjustment are promoted while curbing of resolution decrease due to execution of only optical brightness adjustment is promoted. A switching unit that performs, in response to change in an indication value indicating the brightness of a captured image obtained by an imaging device, switching between optical brightness adjustment that is brightness adjustment according to an iris and electronic brightness adjustment that is brightness adjustment according to application of a gain depending on the indication value to the captured image, and a first delay unit that delays change in the gain with respect to change in the indication value in the electronic brightness adjustment are included.

14 Claims, 15 Drawing Sheets

(51) Int. Cl.
*A61B 1/06* (2006.01)
*H04N 23/71* (2023.01)
*H04N 23/73* (2023.01)

(58) Field of Classification Search
CPC ....... A61B 1/042; A61B 1/043; A61B 1/0684; A61B 1/07; A61B 1/045; H04N 23/71; H04N 23/73; H04N 23/663; H04N 23/667; H04N 23/72; H04N 23/75; H04N 23/76; G03B 7/095
See application file for complete search history.

(56) References Cited

U.S. PATENT DOCUMENTS

| | | | | |
|---|---|---|---|---|
| 2007/0024741 A1* | 2/2007 | Moriya | ................... | H04N 23/72 348/363 |
| 2007/0182836 A1* | 8/2007 | Chino | ................... | H04N 25/00 348/E9.01 |
| 2013/0194469 A1* | 8/2013 | Nakata | ................... | H04N 9/68 348/300 |
| 2016/0373636 A1* | 12/2016 | Hamada | ................ | H04N 23/71 |
| 2019/0086766 A1* | 3/2019 | Paliy | ................... | H04N 23/75 |
| 2019/0253601 A1* | 8/2019 | Qu | ......................... | H04N 23/76 |
| 2021/0218873 A1* | 7/2021 | Ito | .......................... | H04N 23/76 |

FOREIGN PATENT DOCUMENTS

| | | | | |
|---|---|---|---|---|
| JP | 2006352715 A | | 12/2006 | |
| JP | 2013-031010 A | | 2/2013 | |
| JP | 2013-047766 A | | 3/2013 | |
| JP | 2013-085088 A | | 5/2013 | |
| JP | 2015-111746 A | | 6/2015 | |
| JP | 2016-184874 A | | 10/2016 | |
| JP | 2016184874 A | * | 10/2016 | ........... H04N 5/2353 |
| JP | 2017-011389 A | | 1/2017 | |
| JP | 2017-161662 A | | 9/2017 | |
| WO | WO-2013168493 A1 | | 11/2013 | |
| WO | WO-2018173725 A1 | | 9/2018 | |

* cited by examiner

SIGNAL PROCESSING DEVICE, IMAGING DEVICE, AND SIGNAL PROCESSING METHOD

CROSS REFERENCE TO RELATED APPLICATIONS

This application is a U.S. National Phase of International Patent Application No. PCT/JP2020/007431 filed on Feb. 25, 2020, which claims priority benefit of Japanese Patent Application No. JP 2019-066240 filed in the Japan Patent Office on Mar. 29, 2019. Each of the above-referenced applications is hereby incorporated herein by reference in its entirety.

TECHNICAL FIELD

The present technology relates to a signal processing device, an imaging device, and a signal processing method, and particularly, to a technical field with respect to adjustment of the brightness of a captured image.

BACKGROUND ART

With respect to adjustment of the brightness of a captured image, an iris (optical diaphragm) is mainly used for adjustment of a brightness, for example, in a live camera for broadcasting stations. As reasons therefor,
  When an electronic shutter is used, continuity between frames is lost to easily cause a ruffling image, which is not desirable.
  An S/N ratio (signal-to-noise ratio) decreases when a digital gain is increased and a dynamic range is narrowed when a digital gain is decreased.
  An analog gain mostly has a narrow variable range in general.
  A neural density (ND) filter is provided for each light transmissivity and thus it is difficult to continuously change ND filters (although a variable ND filter has recently appeared, brightness decreases by half even when transmissivity is maximized in many cases), and the like may be conceived.
  However, in a case where brightness adjustment according to an iris is performed, when the iris is excessively opened (that is, F value is excessively decreased), the phenomenon that resolution abruptly decreases halfway is seen in many lenses. In a broadcasting B4 mount lens, in general, the resolution is maximized at about F4.0 and abruptly decreases therefrom over F1.8 of opening.
  To prevent such resolution decrease, it is conceived that, when an F value is not more than a certain threshold value F_th, brightness is adjusted by maintaining the F value of a lens (F_th) and changing a gain of a captured image.
As a specific example, a brightness indication operation performed by a user may be an F value indication operation as before, but as internal processing, an iris is controlled when an F value indication value is greater than the threshold value F_th, and the gain is increased while the F value is fixed to F_th when the F value indication value is equal to or less than F-_th.
  PTL 1 described below discloses a technology in which a user inputs position information of a volume for which a brightness will be indicated, an amplification factor is fixed and an iris opening diameter is controlled such that it becomes a value changing in response to the position information when the position information is within an iris control region, and the iris opening diameter is fixed and the amplification factor is controlled such that it becomes a value changing in response to the position information when the position information is within an amplification factor control region.
  When brightness adjustment according to the iris is assumed to be "optical brightness adjustment" and brightness adjustment according to a gain is assumed to be "electronic brightness adjustment," the technology disclosed in PTL 1 can be called switching between optical brightness adjustment and electronic brightness adjustment in response to the size of a brightness indication value in other words.

CITATION LIST

Patent Literature

[PTL 1]
  JP 2015-111746 A

SUMMARY

Technical Problem

However, when a method of switching between optical brightness adjustment and electronic brightness adjustment is employed, a phenomenon that a speed of change of brightness abruptly increases or decreases at a timing of switching between them occurs. Generation of such a brightness change speed difference is caused by a difference between response characteristics with respect to change in an indication value between the iris and the gain.
  When a brightness change speed difference is generated as described above, a user or an output image observer is caused to feel discomfort.
In addition, for the user, difficulty of the operation of adjusting a brightness such that it does not abruptly change increases to cause deterioration of operability with respect to brightness adjustment.
  Accordingly, an object of the present technology is to mitigate a discomfort of a user or an output image observer during brightness adjustment switching and to promote curbing of deterioration in operability with respect to brightness adjustment while promoting curbing of resolution decrease due to execution of only optical brightness adjustment.

Solution to Problem

A signal processing device according to the present technology includes a switching unit that performs, in response to change in an indication value indicating the brightness of a captured image obtained by an imaging device, control of switching between optical brightness adjustment that is brightness adjustment according to an iris and electronic brightness adjustment that is brightness adjustment according to application of a gain depending on the indication value to the captured image, and a first delay unit that delays change in the gain with respect to change in the indication value in the electronic brightness adjustment.
By delaying change in the gain with respect to change in the indication value in electronic brightness adjustment, prevention of abrupt change in a degree of change in brightness is promoted even when the indication value has changed to be a threshold value or less and thus brightness adjustment has switched from optical brightness adjustment to electronic brightness adjustment.

In the aforementioned signal processing device according to the present technology, a configuration in which the indication value is a target value of an F value may be conceived.

Accordingly, it is not necessary to convert a brightness indication value other than the F value into an F value in execution of optical brightness adjustment.

In the aforementioned signal processing device according to the present technology, a configuration in which the switching unit performs the switching control on the basis of a result of comparison between the indication value and a threshold value may be conceived.

Accordingly, optical brightness adjustment is performed having a predetermined F value as a limit.

In the aforementioned signal processing device according to the present technology, a configuration in which the indication value is a target value of an F value, and the switching unit performs switching control such that optical brightness adjustment is performed on a side on which the target value of the F value is large and electronic brightness adjustment is performed on a side on which the target value of the F value is small, with respect to the threshold value may be conceived.

That is, optical brightness adjustment is performed in a region where the F value is large and resolution is high and electronic brightness adjustment instead of optical brightness adjustment is performed in a region where the F value is small and resolution tends to be low.

In the aforementioned signal processing device according to the present technology, a configuration in which the first delay unit changes a gain change speed within a period in which the gain is changed in the electronic brightness adjustment may be conceived.

Accordingly, it is possible to approximate brightness change characteristics according to electronic brightness adjustment to brightness change characteristics according to optical brightness adjustment.

In the aforementioned signal processing device according to the present technology, a configuration in which the first delay unit suppresses a gain change speed to a predetermined speed or less in electronic brightness adjustment may be conceived. There is an upper limit in a speed of change of brightness in optical brightness adjustment due to characteristics of the iris.

In the aforementioned signal processing device according to the present technology, a configuration in which the first delay unit delays the gain according to delay characteristics imitating inertia in the electronic brightness adjustment may be conceived.

Accordingly, it is possible to cause brightness change characteristics according to electronic brightness adjustment to be change characteristics to which inertia acting on the iris has been added.

In the aforementioned signal processing device according to the present technology, a configuration in which the switching unit is configured to be able to switch between a switching mode in which control of switching between optical brightness adjustment and electronic brightness adjustment is performed in response to change in the indication value and a non-switching mode in which switching control is not performed with respect to change in the indication value and optical brightness adjustment is executed may be conceived.

Accordingly, the F value can be decreased to a minimum value.

In the aforementioned signal processing device according to the present technology, a configuration in which the switching unit performs switching between the switching mode and the non-switching mode on the basis of an operation may be conceived.

Accordingly, it is possible to perform switching between the switching mode and the non-switching mode on the basis of an intention of a user.

In the aforementioned signal processing device according to the present technology, a configuration in which the switching unit performs switching between the switching mode and the non-switching mode on the basis of an operation of the remote controller may be conceived.

Accordingly, a burden of operation of switching between the switching mode and the non-switching mode is not imposed on a cameraman.

In the aforementioned signal processing device according to the present technology, a configuration in which the first delay unit is configured to be able to change delay characteristics of the gain in the electronic brightness adjustment may be conceived. Accordingly, it is possible to change brightness change characteristics according to electronic brightness adjustment to characteristics corresponding to brightness change characteristics according to optical brightness adjustment in response to a case in which iris characteristics change due to a certain circumstance.

In the aforementioned signal processing device according to the present technology, a configuration in which the imaging device is a lens interchangeable type imaging device, and the first delay unit delays change in the gain according to delay characteristics based on information acquired from a lens device mounted in the imaging device may be conceived.

Accordingly, it is possible to cause change characteristics of brightness according to electronic brightness adjustment to be characteristics suitable for a lens device in response to a case in which iris characteristics vary according to lens devices to be mounted.

In the aforementioned signal processing device according to the present technology, a configuration including a second delay unit that delays change in the F value with respect to change in the indication value in optical brightness adjustment may be conceived.

Accordingly, it is possible to cause change characteristics of the F value with respect to change in the indication value to be desired characteristics.

In addition, an imaging device according to the present technology includes an imaging element that receives incident light through an iris to acquire a captured image, a switching unit that performs, in response to change in an indication value indicating the brightness of the captured image, switching between optical brightness adjustment that is brightness adjustment according to the iris and electronic brightness adjustment that is brightness adjustment according to application of a gain depending on the indication value to the captured image, and a first delay unit that delays change in the gain with respect to change in the indication value in the electronic brightness adjustment.

The same operation as that of the aforementioned signal processing device according to the present technology can be acquired by the imaging device according to the present technology.

Further, a signal processing method according to the present technology is a signal processing method that performs, in response to change in an indication value indicating the brightness of a captured image obtained by an imaging device, switching between optical brightness adjustment that is brightness adjustment according to an iris and electronic brightness adjustment that is brightness adjustment according to application of a gain depending on the indication value to the captured image, and delays change in the gain with respect to change in the indication value in the electronic brightness adjustment.

The same operation as that of the aforementioned signal processing method according to the present technology can also be obtained by this signal processing method.

DESCRIPTION OF EMBODIMENTS

Hereinafter, embodiments will be described in the following order.
<1. Configuration of imaging system>
<2. Brightness adjustment method as embodiment>
[First example of delay characteristics]
[Second example of delay characteristics]
[Third example of delay characteristics]
[With respect to mode switching]
<3. Modified examples>
[3-1. First modified example]
[3-2. Second modified example]
[3-3. Other modified examples]
<4. Conclusion of embodiments>
<5. Application Examples>
<6. Present technology>

1. Configuration of Imaging System

Figure 1:
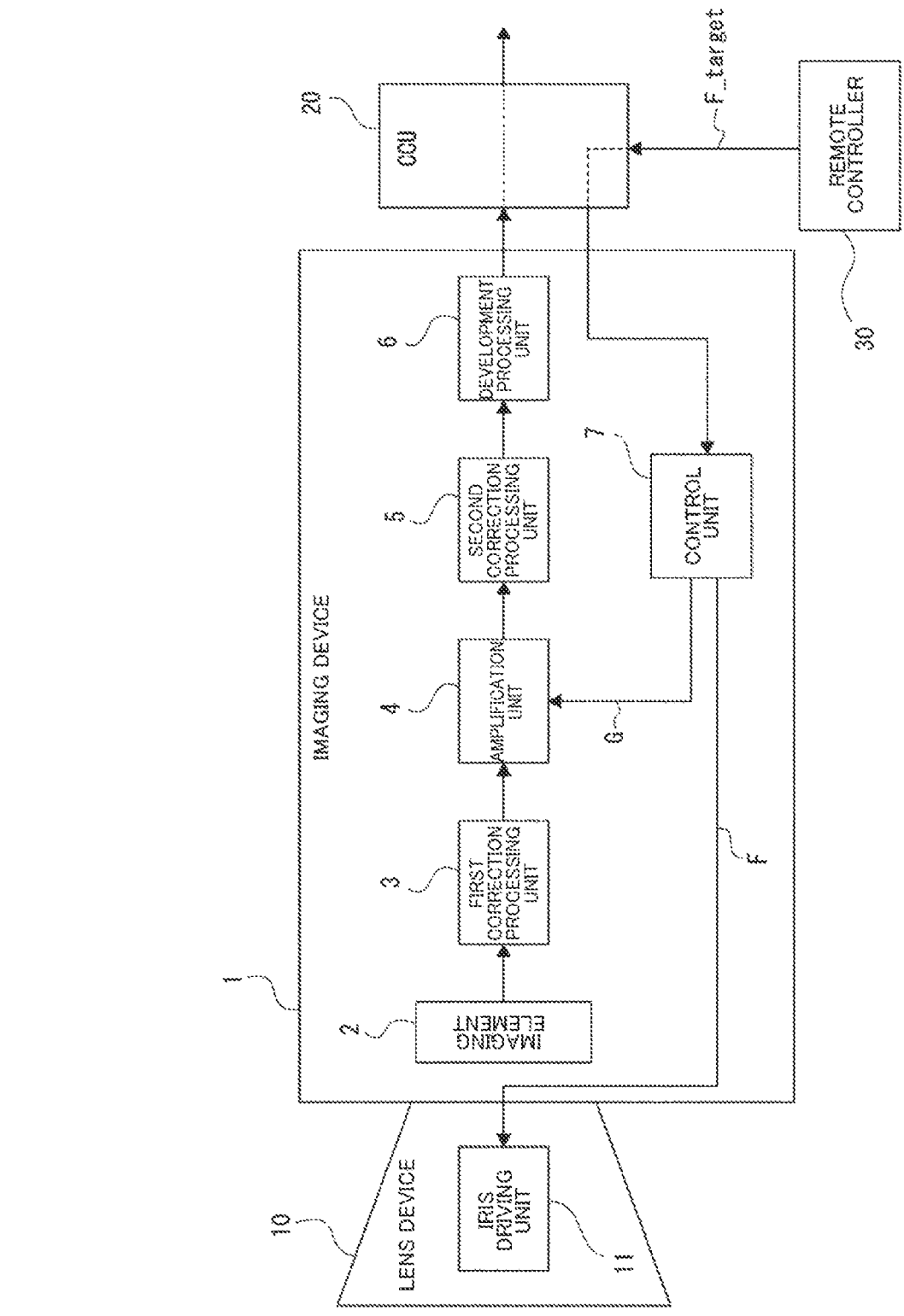
FIG. 1 is a diagram illustrating a configuration example of an imaging system including an imaging device according to the present technology.

FIG. 1 is a diagram illustrating a configuration example of an imaging system including an imaging device 1 that is an embodiment of a signal processing device according to the present technology.

The imaging system in the present embodiment is, for example, a broadcasting live camera system and is used inside a broadcasting station or outside in the case of sports broadcasting. As illustrated, the imaging system includes the imaging device 1, a lens device 10, a camera control unit (CCU) 20, and a remote controller 30.

The lens device 10 is detachably mounted on the imaging device 1 through a mounting part that is not illustrated. In the imaging system, the imaging device 1 having the lens device 10 mounted thereon is mainly used by a user as a cameraman.

Further, the CCU 20 and the remote controller 30 are disposed, for example, in a room separate from a studio in a broadcasting station or disposed inside an outside broadcast van when used outside and mainly used by a user such as a video engineer.

Here, although the broadcasting live camera system generally employs a configuration including a plurality of sets of the imaging device 1, the CCU 20, and the remote controller 30, only one of the plurality of sets is illustrated here for convenience of illustration.

The lens device 10 is, for example, a lens device based on the B4 mount standard and includes lenses such as a cover lens, a zoom lens, and a focus lens, an iris (optical diaphragm), and the like as optical components. In addition, the lens device 10 includes an iris driving unit 11 having an actuator such as a motor for driving the iris, for example.

The lens device 10 concentrates light (incident light) from a subject and guides the concentrated light to an imaging element 2 which will be described later in a state in which it is mounted on the imaging device 1. Here, the incident light from the subject is received by the imaging element 2 through the iris.

The imaging device 1 includes the imaging element 2, a first correction processing unit 3, an amplification unit 4, a second correction processing unit 5, a development processing unit 6, and a control unit 7.

The imaging element 2 is, for example, an image sensor such as a complementary metal oxide semiconductor (CMOS) type or a charge coupled device (CCD) type, photoelectrically converts received light, executes, for example, correlated double sampling (CDS) processing, automatic gain control (AGC) processing, and the like on an electrical signal obtained by photoelectric conversion, and additionally performs analog/digital (A/D) conversion processing. Then, a captured image signal (captured image data) as digital data is output to the first correction processing unit 3 at the following stage.

The first correction processing unit 3 performs image correction processing, such as defective pixel correction, ambient light amount decrease correction, and lens aberration correction, on the captured image signal from the imaging element 2.

The amplification unit 4 amplifies the captured image signal input through the first correction processing unit 3 on the basis of a gain G indicated by the control unit 7. Amplification of the captured image signal by the amplification unit 4 is performed as, for example, amplification of a luminance value. Here, when the gain G=1, a signal amplification factor of the amplification unit 4 is 1, and thus the brightness of a captured image does not change between before and after processing of the amplification unit 4.

The second correction processing unit 5 performs predetermined image correction processing different from image correction processing in the first correction processing unit 3 on the captured image signal input through the amplification unit 4.

The development processing unit 6 performs predetermined image signal processing, for example, γ correction processing, on the captured image signal input through the second correction processing unit 5.

In the imaging system of this example, the captured image signal processed by the development processing unit 6 is input to the CCU 20 as an output image signal of the imaging device 1.

The CCU 20 is configured to be able to perform wired communication via a cable or wireless communication with the imaging device 1, transfers the captured image signal output from the imaging device 1 to, for example, an external device such as a video editing device which is not illustrated, and controls the imaging device 1 on the basis of an input signal and the like from the remote controller 30. Here, the video editing device that processes an output image from the CCU 20 can switch between captured images from a plurality of imaging devices 1 or combine a plurality of captured images in the case of a system including a plurality of imaging devices 1 and CCUs 20.

The control unit 7 includes a microcomputer (arithmetic operation processing device) including, for example, a central processing unit (CPU), a read only memory (ROM), a random access memory (RAM), and the like and controls operation of the imaging device 1, for example, by executing processing according to a program stored in the ROM.
The control unit 7 controls various operations of the imaging device 1 on the basis of an operation input from the remote controller 30.

Figure 2:
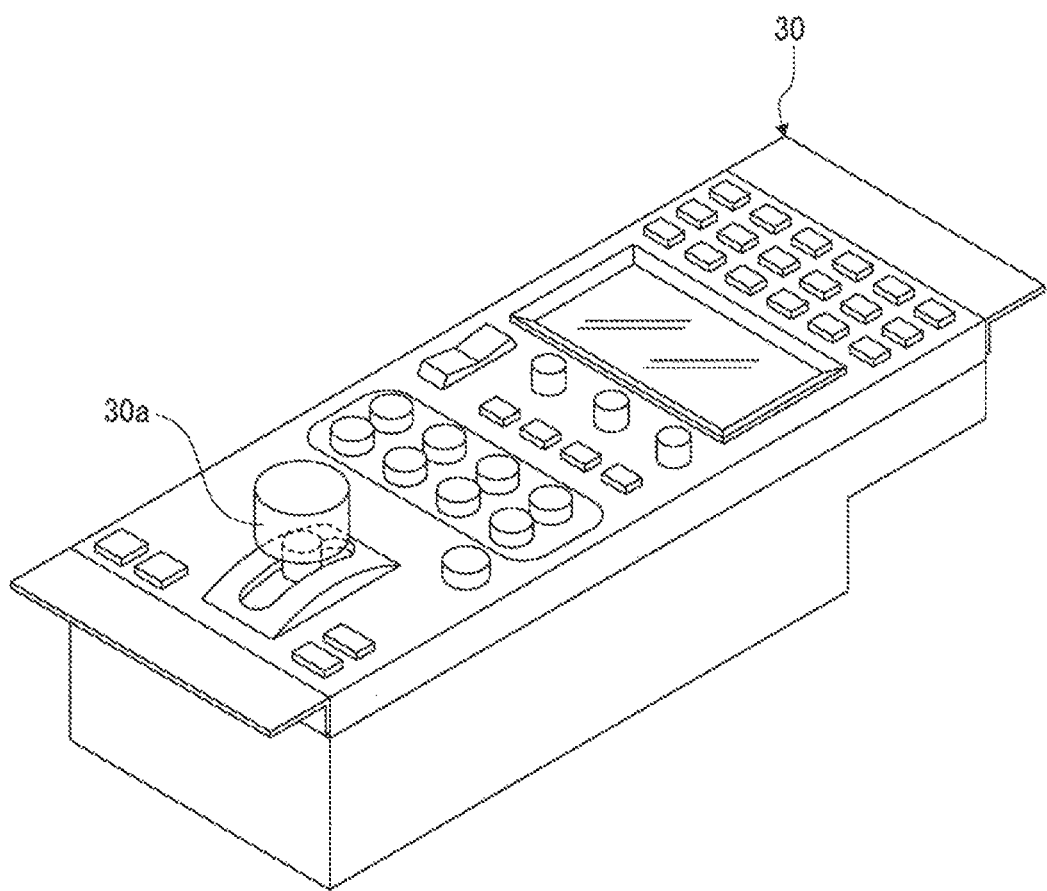
FIG. 2 is a perspective view illustrating a configuration example of the exterior of a remote controller included in an imaging system of an embodiment.

FIG. 2 is a perspective view illustrating a configuration example of the exterior of the remote controller 30.
As illustrated, operators such as a plurality of buttons and knobs are formed in the remote controller 30. Particularly, an adjustment operator 30a for performing brightness adjustment of a captured image is formed in the remote controller 30.

In this example, the adjustment operator 30a is, for example, a lever type operator, and an indication value of the brightness of a captured image can be changed by an operation of rotating the adjustment operator 30a. Specifically, the indication value indicates a darkest brightness (a maximum value in the case of an F value which will be described later) at a position at which the adjustment operator 30a reaches one end and indicates a brightest brightness (a minimum value in the case of the F value which will be described later) at a position at which the adjustment operator 30a reaches the other end. In addition, the indication value changes by monotonically increasing or monotonically decreasing (e.g., linearly) from one end toward the other end.

Meanwhile, the adjustment operator 30a is not limited to a lever type operator and can be an operator of other types, for example, a rotary type operator and a slide type operator.

Here, it is assumed that indication of the brightness of a captured image is performed as indication of an F value in the imaging system of this example. Accordingly, the remote controller 30 in this example outputs an operation state of the adjustment operator 30a, specifically, a target value (hereinafter denoted as "target value F_target") of an F value in response to a rotation angle of the adjustment operator 30a to the CCU 20 as a brightness indication value. Here, an F value may be a value indicating a brightness corresponding to an F value in response to change in an effective aperture of a lens according to driving of the iris and may not necessarily be the F value itself in response to change in the effective aperture of the lens according to driving of the iris. The CCU 20 transfers the target value F_target input through the remote controller 30 to the control unit 7 in the imaging device 1.

Meanwhile, although an example in which the remote controller 30 outputs the target value F_target has been described above, a configuration in which the CCU 20 generates the target value F_target on the basis of an operation input signal (e.g., a signal indicating a value in response to a rotation angle of the adjustment operator 30a) from the remote controller 30 and transfers the target value F_target to the control unit 7 can also be employed.

In FIG. 1, the control unit 7 outputs the F value to the iris driving unit 11 and outputs the gain G to the amplification unit 4 to adjust the brightness of the captured image on the basis of the target value F_target input from the CCU 20. Specific processing executed by the control unit 7 to adjust the brightness of the captured image will be described in detail below.

Meanwhile, although the imaging device 1 performs correction processing (processing of the first correction processing unit 3 and the second correction processing unit 5) and development processing (processing of the development processing unit 6) in FIG. 1, some processing may be omitted or a processing order may be changed.

2. Brightness Adjustment Method as Embodiment

Specific processing performed by the control unit 7 to adjust the brightness of a captured image will be described. Meanwhile, in the following description, the brightness of a captured image may be simply abbreviated as "brightness."
In brightness adjustment of this example, in response to change in an indication value (target value F_target in this example) indicating brightness, switching between "optical brightness adjustment" that is brightness adjustment according to the iris and "electronic brightness adjustment" that is brightness adjustment according to application of a gain depending on the indication value to a captured image is performed.
As described above, the target value F_target of the F value is input to the control unit 7 as a brightness indication value in response to operation of the adjustment operator 30a in the remote controller 30 in this example. In this example, a threshold value F_th for this target value F_target of the F value as a brightness indication value is fixed, and the control unit 7 performs switching between optical brightness adjustment and electronic brightness adjustment on the basis of a result of comparison between the target value F_target and the threshold value F_th.

Figure 3:
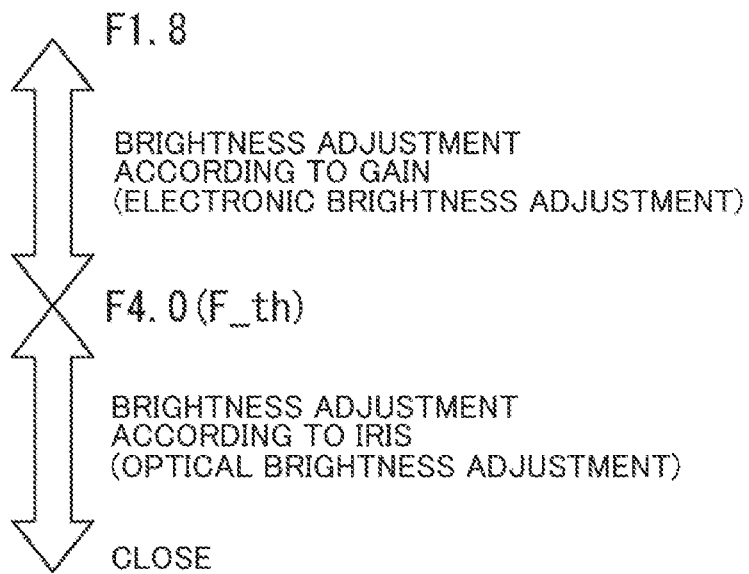
FIG. 3 is a conceptual diagram of an example of switching between optical brightness adjustment and electronic brightness adjustment.
Figure 4:
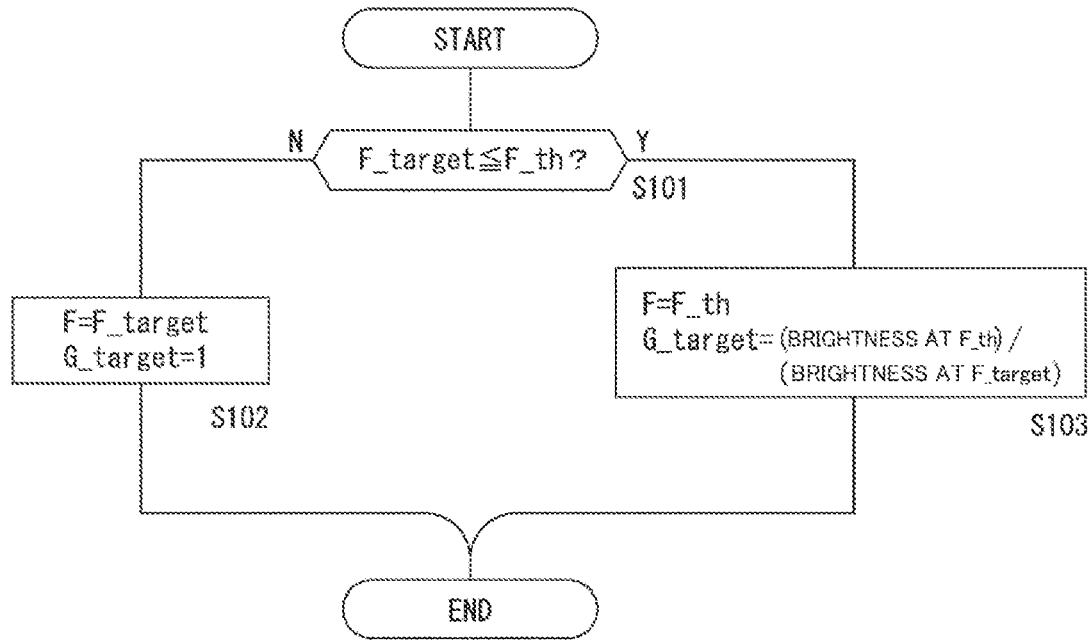
FIG. 4 is a flowchart illustrating an example of processing of switching between optical brightness adjustment and electronic brightness adjustment.

FIG. 3 and FIG. 4 are diagrams for describing an example of switching between optical brightness adjustment and electronic brightness adjustment, FIG. 3 is a conceptual diagram of an example of this switching, and FIG. 4 illustrates an example of processing executed by the control unit 7 for this switching.
As illustrated in FIG. 3, a minimum value of the F value is, for example, F1.8, and F4.0 is set as the threshold value F_th (refer to FIG. 3). The control unit 7 determines whether the target value F_target is the threshold value F_th or less (step S101 in FIG. 4), and if the target value F_target is not the threshold value F_th or less, sets an F value indicated to the iris driving unit 11 to the target value F_target and sets a target value G_target of a gain G indicated to the amplification unit 4 to "1" (step S102).

In this manner, when the target value F_target is not the threshold value F_th or less, brightness adjustment according to the gain G is not performed because the target value G_target is set to "1", whereas brightness adjustment according to the iris is performed because the F value is set to the target value F_target (refer to FIG. 3). That is, when the target value F_target is greater than the threshold value F_th, electronic brightness adjustment is not performed and optical brightness adjustment is performed.

On the other hand, when the target value F_target is the threshold value F_th or less, the control unit 7 sets the F value indicated to the iris driving unit 11 to the threshold value F_th and sets the target value G_target of the gain G to a value depending on a difference between a brightness at the target value F_target and a brightness at the threshold value F_th, specifically, a value of (brightness at the target value F_target)/(brightness at the threshold value F_th) (step S103). That is, when the target value F_target is the threshold value F_th or less, brightness adjustment according to the iris is not performed because the F value is set to the threshold value F_th, whereas brightness adjustment according to the gain G is performed because the target value G_target changes depending on the size of the target value F_target of the F value (refer to FIG. 3).

Here, the brightness at the target value F_target is inversely proportional to "F_target×F_target" and the brightness at the threshold value F_th is inversely proportional to "F_th×F_th" with respect to processing of step S103. Accordingly, the target value G_target of the gain G in step S103 is obtained according to G_target=(F_th×F_th)/(F_target×F_target).

By performing brightness adjustment switching based on the aforementioned threshold value F_th, optical brightness adjustment is performed having a predetermined F value as a limit.

Accordingly, it is possible to promote curbing of resolution decrease occurring when only optical brightness adjustment is performed.

Here, since optical brightness adjustment requires driving of a mechanical part (diaphragm blade and the like) in the iris, change in brightness tends to be gentle with respect to change in the target value F_target.

Figure 5:
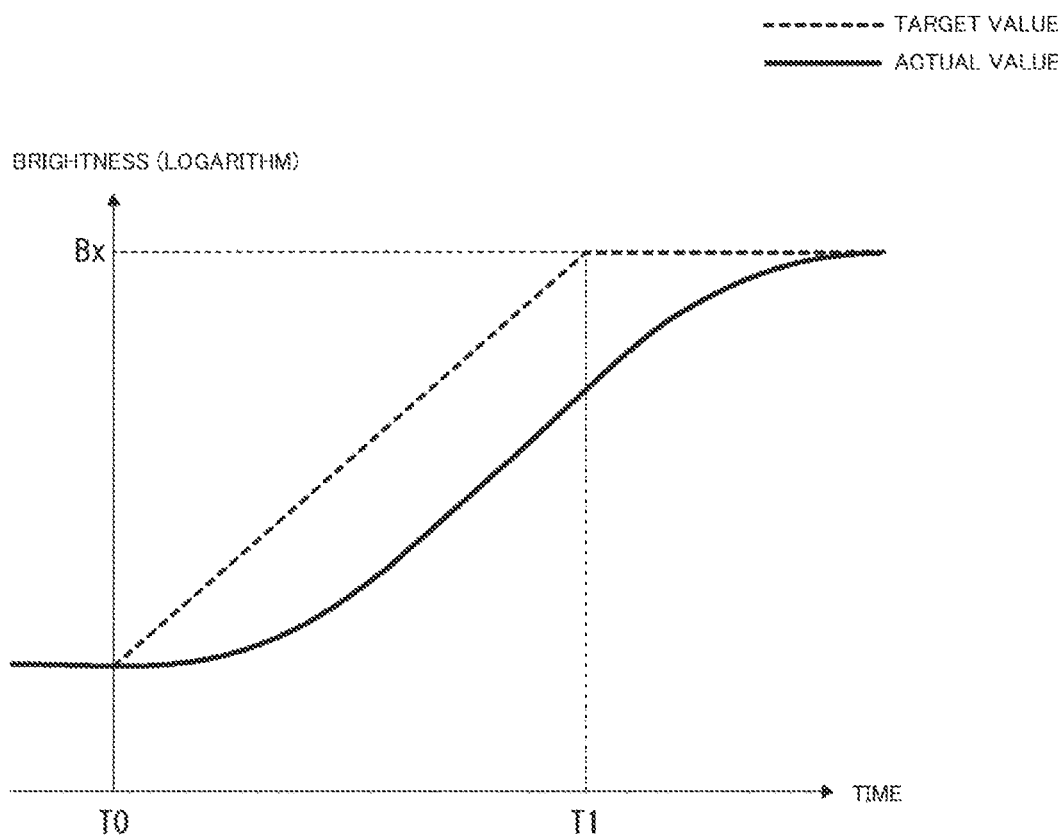
FIG. 5 is a diagram schematically representing brightness change characteristics when an iris is used.

FIG. 5 schematically represents change characteristics (thick solid line in the figure) of brightness with respect to the target value F_target (thick broken line in the figure) when the iris is used. Specifically, the illustrated example represents change characteristics when the target value F_target has been changed to a value corresponding to a brightness Bx at a specific speed from a point in time T0 to a point in time T1.

When the iris is used, brightness barely changes in a starting period immediately after the point in time T0 and thus a delay with respect to the target value F_target occurs according to the influence of inertia acting on the mechanical part. After the starting period, a speed of change of brightness gradually increases to reach a change speed approximately equal to a change speed of the target value F_target. Thereafter, the aperture in the iris continuously extends according to the influence of inertia and brightness also continuously changes even when change in the target value F_target ends at the point in time T1. The speed of change of brightness slowly decreases after a certain time from the point in time T1, and then change in brightness ends.

In this manner, change characteristics of brightness when the iris is used has a delay with respect to change in the target value F_target.

On the other hand, in electronic brightness adjustment, driving of a mechanical part such as the iris is not performed and a delay in brightness change is barely generated with respect to change in the target value F_target.

Accordingly, when switching between optical brightness adjustment and electronic brightness adjustment is performed, a phenomenon that a speed of change of brightness abruptly increases or decreases at a switching timing occurs.

Figure 6A:
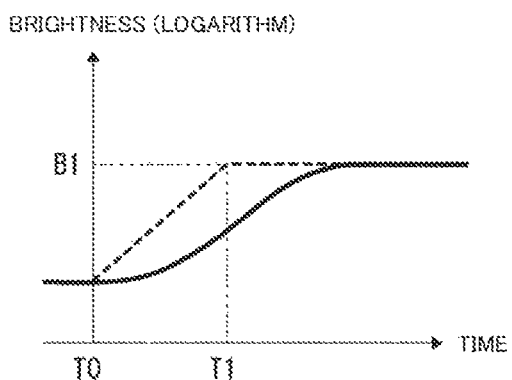
FIGS. 6A, 6B, and 6C are explanatory diagrams with respect to abrupt change in a speed of change of brightness during switching between optical brightness adjustment and electronic brightness adjustment.
Figure 6B:
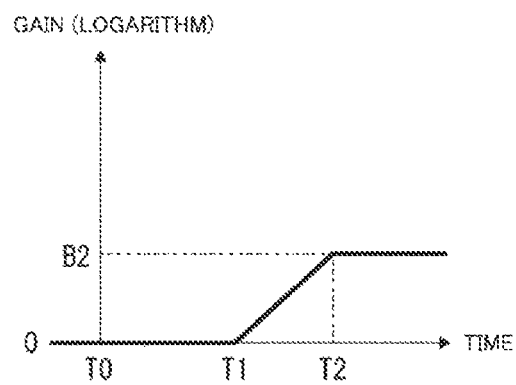
Figure 6C:
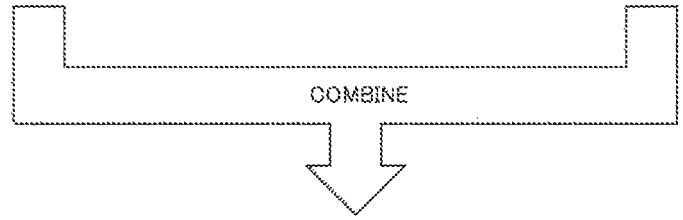
Figure 6C:
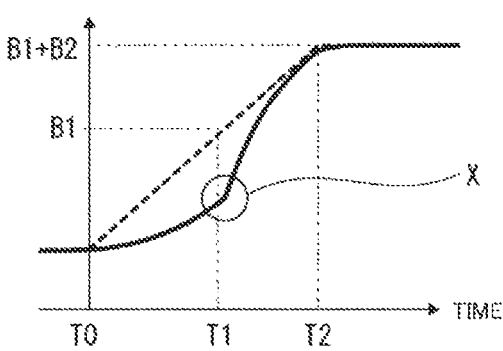

FIGS. 6A, 6B, and 6C are explanatory diagrams with respect to this, and it is assumed that a brightness is changed to B1 according to optical brightness adjustment from a point in time T0 to a point in time T1, as shown in FIG. 6A, and a logarithm of a gain is changed from 0 to B2 according to electronic brightness adjustment from the point in time T1 to a point in time T2, as shown in FIG. 6B. In this case, although change characteristics of brightness from the point in time T0 to the point in time T2 correspond to a combination of these change characteristics of FIG. 6A and FIG. 6B and become characteristics as shown in FIG. 6C, a part in which a speed of change of brightness abruptly changes is generated, as indicated by "X" in the figure, caused by a difference between the change characteristics of FIGS. 6A and FIG. 6B at the point in time T1 that is a timing of switching between optical brightness adjustment and electronic brightness adjustment.

Such a brightness change speed difference causes a user or an output image observer to feel discomfort. In addition, for the user, difficulty of the operation of adjusting a brightness such that it does not abruptly change increases to cause deterioration of operability with respect to brightness adjustment.

Accordingly, in the present embodiment, change in the gain G is delayed with respect to change in a brightness indication value.

Figure 7:
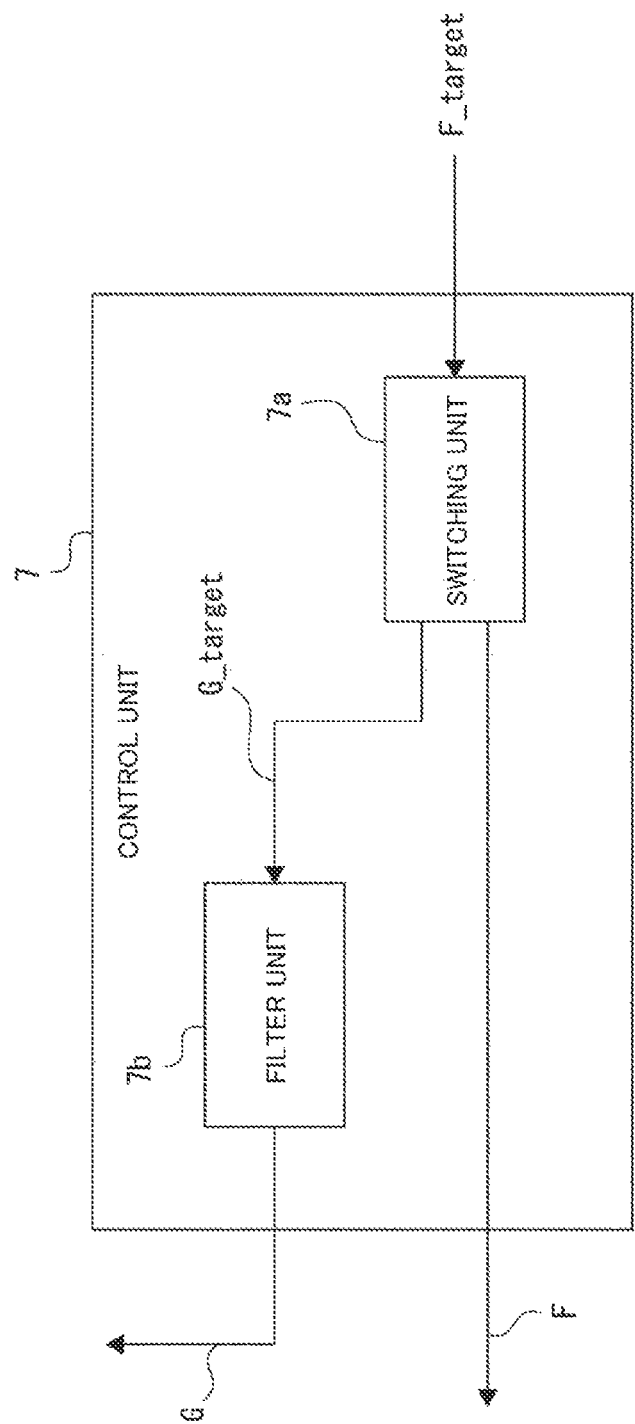
FIG. 7 is a functional block diagram representing a function for brightness adjustment in an embodiment.

Accordingly, the control unit 7 has a function as a filter unit 7b shown in FIG. 7. While FIG. 7 is a functional block diagram representing a function of the control unit 7 for brightness adjustment, the control unit 7 has a function as a switching unit 7a and the function as the filter unit 7b, as illustrated.

The switching unit 7a switches between optical brightness adjustment and electronic brightness adjustment by performing processing shown in FIG. 4.

The filter unit 7b is a digital filter realized by software processing and serves as a delay filter that delays the target value G_target of the gain G input from the switching unit 7a. The target value G_target delayed by this filter unit 7b is output to the amplification unit 4 as the gain G.

Here, although various examples may be conceived with respect to filter characteristics (delay characteristics) of the filter unit 7b, first to third examples will be given as a part thereof below.

First Example of Delay Characteristics

The first example is an example in which a difference between the target value G_target and a current value G(t) of the gain G is multiplied by a proportional coefficient p and a multiplication result is added to the current value G(t) of the gain G, as represented by the formula below.

$$G(t+1)=G(t)+(G\_target-G(t))\times p$$

Second Example of Delay Characteristics

The second example is an example of limiting a change speed.
There is an upper limit in a change speed in an actual iris. Accordingly, an upper limit is also provided to a change speed in delay characteristics according to the filter unit 7b such that the delay characteristics further approximate characteristics of the iris.
Although the method of adding a value obtained by multiplying a difference between the target value G_target and the current value G(t) of the gain G by the proportional coefficient p to the current value G(t) of the gain G is basically used in the second example as in the first example, the value (represented as "ΔG(t)" below) added to G(t) is limited on the basis of an upper limit value ΔG_max of a variation of the gain G in the second example.
Specifically, ΔG(t) is defined as follows.

$$\Delta G(t) = G\_target - G(t) \times p$$

Then, when $|\Delta G(t)| > \Delta G\_max$, $$\Delta G'(t)G'(t) = \Delta G\_max \times \Delta G(t)/|\Delta G(t)|$$

and, when $|\Delta G'(t)| \leq \Delta G\_max$, $$\Delta G'(t) = \Delta G(t),$$

and thus $G(t+1) = G(t) + \Delta G'(t)$ is obtained.

Third Example of Delay Characteristics

The third example considers inertia acting on the iris. The actual iris is driven having a weight and thus it has inertia and is barely accelerated when it starts to move. Accordingly, delay characteristics imitating the inertia acting on the iris are set such that they approximate the characteristics of the iris.
Specifically, a current variation of the gain G is set to Gs(t) and a variation of the gain G at the next time is set to Gs(t+1). Then, $$F(t) = (G\_target - G(t)) \times p - Gs(t) \times d \text{ and}$$

$$Gs(t+1) = Gs(t) + F(t)$$

and thus $G(t+1) = G(t) + Gs(t+1)$ is obtained.

Figure 8A:
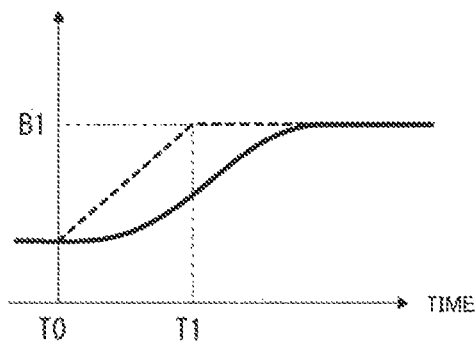
FIGS. 8A, 8B, and 8C are diagrams for describing an effect of delaying of a gain.
Figure 8B:
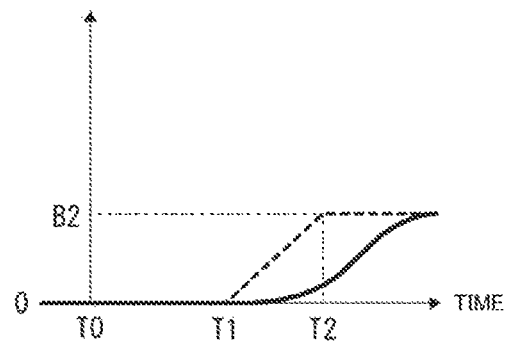
Figure 8C:
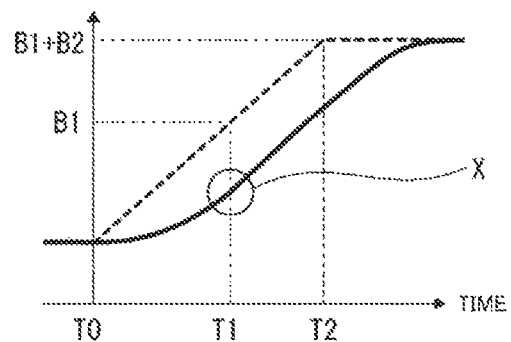

FIGS. 8A, 8B, and 8C is a are diagrams for describing an effect of delaying of the gain G, and the gain G responds to change in the target value F_target with a delay in this example, as can be ascertained from a comparison between FIGS. 6B and 8B.
In this example, change characteristics of the gain G with respect to change in the target value F_target, that is, change characteristics of a brightness in electronic brightness adjustment become curved characteristics instead of linear characteristics even in a case where any of the aforementioned first to third example is employed. Specifically, even in a case where any of the first to third example is employed, the change speed of the gain G gradually changes and thus a change state of the gain G becomes a curved change state within a period (a period after the point in time T1 in the example of the figure) in which the gain G is changed in optical brightness adjustment.

Particularly, in a case where the third example considering inertia is employed, a response period in which the gain G barely changes with respect to change in the target value F_target is acquired near the point in time T1 that is a timing of switching to electronic brightness adjustment.
In addition, although change characteristics of a brightness according to brightness adjustment of this example become change characteristics as shown in FIG. 8C which correspond to a combination of change characteristics of brightness according to optical brightness adjustment shown in FIG. 8A and change characteristics of brightness according to electronic brightness adjustment shown in FIG. 8B, abrupt change in the speed of change of brightness, as represented in FIG. 6C, is curbed in this example because brightness change characteristics according to electronic brightness adjustment approximate brightness change characteristics according to optical brightness adjustment by providing the filter unit 7b shown in FIG. 7, and thus change in brightness can be smoothened even when switching between optical brightness adjustment and electronic brightness adjustment is performed (refer to a part represented by "X" in FIG. 8C).
Here, the filter unit 7b functions as a filter having a delay time and thus it also serves as a low pass filter. Since the filter unit 7b also functions as a low pass filter in this manner, prevention of change in the value of the gain G little by little is promoted even when the adjustment operator 30a is operated little by little in this example. That is, prevention of change in brightness little by little is promoted.
There is also a case in which, although a user wants to change the target value F_target at a constant speed, the speed changes, for example, due to tremor of a hand, and the like. In such a case, brightness adjustment can be realized according to intention of the user and improvement in operability with respect to brightness adjustment is promoted by curbing a response to operation performed little by little.

[With Respect to Mode Switching]

Here, the control unit 7 in this example is configured to be able to switch between a switching mode in which control of switching between optical brightness adjustment and electronic brightness adjustment as described above is performed and a non-switching mode in which control of switching is not performed and optical brightness adjustment is executed as brightness adjustment modes in response to the target value F_target indicated by operation of the adjustment operator 30a. Between these modes, the non-switching mode can be referred to as a mode of changing the F value in response to change in the target value F_target even when the target value F_target becomes the threshold value F_th or less in other words.
In this example, the control unit 7 executes switching between the switching mode and the non-switching mode as described above on the basis of operation of the remote controller 30.
For example, the remote controller 30 is provided with an operator, for example, a button or the like, by which switching between the switching mode and the non-switching mode is instructed, and outputs corresponding operation input information to the CCU 20 in response to operation of the operator. This operation input information is transferred to the control unit 7 via the CCU 20.
Here, when the aforementioned non-switching mode is provided such that the F value can be decreased to a minimum value in response to operation of the adjustment operator 30a, the following advantages are obtained.

One advantage is that efficiency of an adjustment work in flange back adjustment (adjustment of a distance from an installation plane of the lens device 10 to an imaging plane) can be promoted. Flange back adjustment is performed while observing blur generated in a captured image, and when the F value cannot be decreased during adjustment, it is difficult to perform flange back adjustment because blur is hardly generated. Accordingly, it is possible to facilitate generation of blur in a captured image and to promote efficiency of the adjustment work by performing switching to the non-switching mode such that the F value can be set to be less than the threshold value F_th.

Another advantage is that response to intention to create an image, such as intention to generate background blur, can be promoted. A user of the imaging system may desire to create fantastic image content with a blurred background, and it is possible to respond to such a desire.

Meanwhile, an operation of switching between the switching mode and the non-switching mode is not limited to the operation of the remote controller 30 and can also be an operation for the imaging device 1.

When the mode switching operation is set as an operation of the remote controller 30, a mode switching operation burden is not imposed on a cameraman.

Here, since the above-described flange back adjustment is performed by the cameraman, it is not desirable to impose an extra operation burden on the cameraman during flange back adjustment in terms of efficiency of the adjustment work. By setting the mode switching operation as an operation of the remote controller 30, it is possible to cause a person other than a cameraman such as a video engineer to perform the mode switching operation to promote reduction in an operation burden on the cameraman during flange back adjustment and to promote efficiency of the adjustment work.

Meanwhile, although not particularly mentioned in the above description, the threshold value F_th used for switching between optical brightness adjustment and electronic brightness adjustment can be caused to be variable, for example, according to operation input, the type of the lens device 10, or the like. A case in which the F value at which resolution starts to decrease changes according to the type or entity of the lens device 10 may also be conceived, and in such a case, the effect of curbing resolution decrease can be improved by varying the threshold value F_th according to the type of the lens device 10, and the like.

3. Modified Examples

[3-1. First Modified Example]

Meanwhile, embodiments are not limited to the aforementioned specific examples and various modified examples may be conceived.

For example, the filter characteristics of the filter unit 7b, that is, delay characteristics of the gain G can be caused to be variable.

As an example, it is conceivable that these delay characteristics are caused to be variable in response to characteristics of the iris in the lens device 10.

Figure 9:
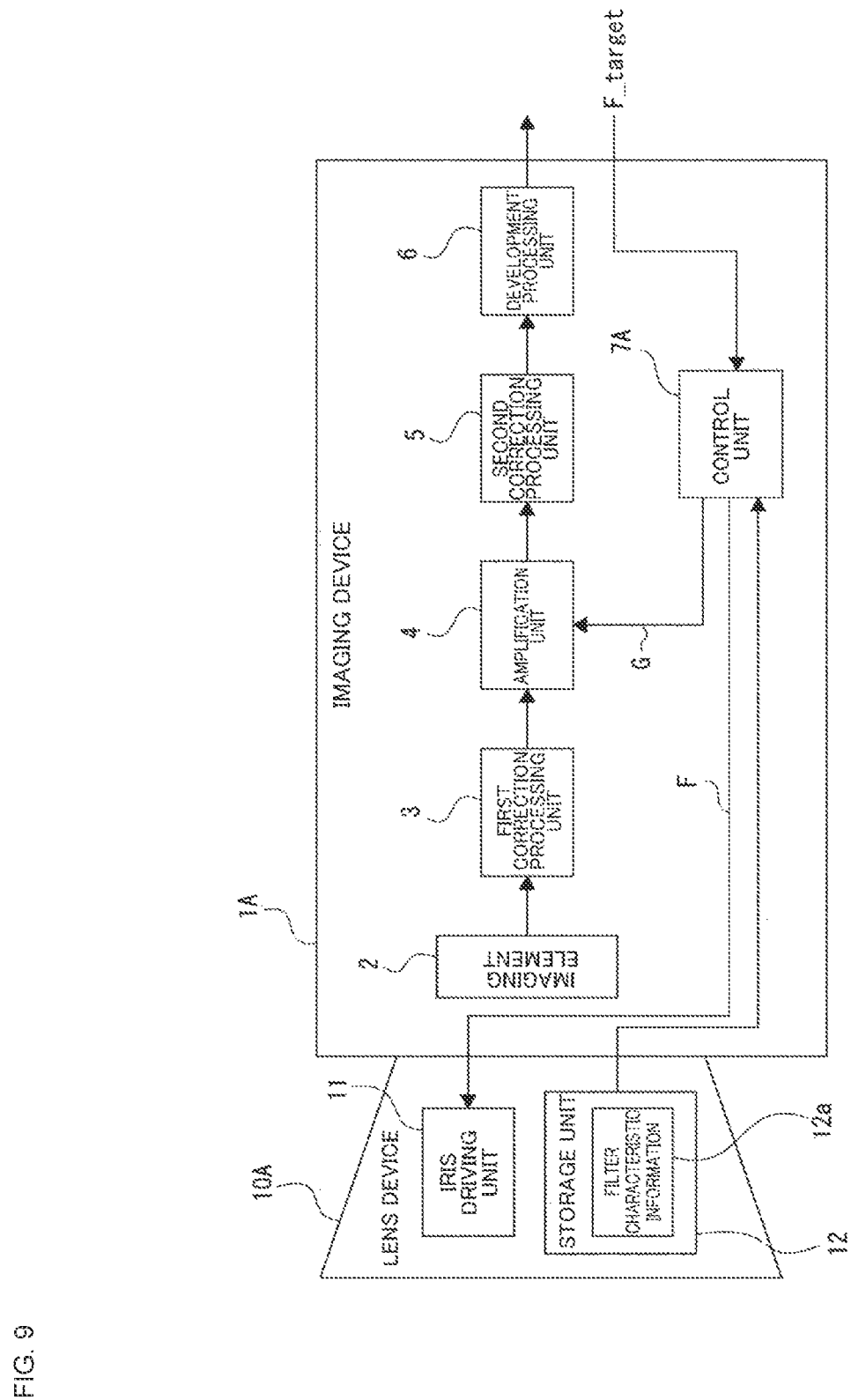
FIG. 9 is a diagram for describing a configuration of an imaging system as a first modified example.

FIG. 9 is a diagram for describing a configuration of an imaging system as a first modified example. Meanwhile, in the following description, parts similar to those that have already been described above will be denoted by the same reference numerals and signs, and description thereof will be omitted.

Here, illustration of the CCU 20 and the remote controller 30 is omitted in FIG. 9.

In the first modified example, a lens device 10A in which information representing the filter characteristics of the filter unit 7b is stored is used. The lens device 10A differs from the lens device 10 in that it includes a storage unit 12 as a nonvolatile memory. The storage unit 12 stores filter characteristic information 12a representing the filter characteristics of the filter unit 7b corresponding to characteristics of an iris of the lens device 10A.

In the imaging system in this case, the imaging device 1A is provided instead of the imaging device 1. The imaging device 1A differs from the imaging device 1 in that a control unit 7A is provided instead of the control unit 7. The control unit 7A acquires the filter characteristic information 12a from the storage unit 12 of the lens device 10A mounted on the imaging device 1A and delays the target value G_target according to delay characteristics (i.e., the filter characteristics of the filter unit 7b) in accordance with the acquired filter characteristic information 12a in electronic brightness adjustment.

Accordingly, change characteristics of brightness according to electronic brightness adjustment can be caused to be characteristics suitable for the lens device in response to a case in which iris characteristics vary according to the lens device 10A to be mounted. That is, it is possible to promote mitigation of a discomfort of a user during brightness adjustment switching and curbing of deterioration in operability with respect to brightness adjustment in response to a case in which iris characteristics vary according to a lens device to be mounted.

Here, as a specific example of the filter characteristic information 12a, information such as a tap coefficient and the number of taps may be conceived, for example, when a finite impulse response (FIR) filter is used as the filter unit 7b.

An example in which the delay characteristics of the gain G is changed in response to the iris characteristics is not limited to the aforementioned example in which the filter characteristic information 12a is stored in the lens device 10A. For example, a configuration in which entity identification information (e.g., information such as the model number and the manufacture's serial number of the lens device 10A) for each lens device 10A is stored in the storage unit 12 and the control unit 7A delays the target value G_target according to delay characteristics corresponding to the entity identification information acquired from the lens device 10A can also be employed.

In this case, in the imaging device 1A, a predetermined storage means (e.g., a memory or the like included in the control unit 7A) is caused to store table information representing a corresponding relationship between entity identification information and delay characteristics, and the control unit 7A performs processing of delaying the target value G_target according to delay characteristics specified from the table information on the basis of acquired entity identification information.

Meanwhile, although an example in which the delay characteristics of the gain G are caused to be variable for each lens device 10A to be mounted has been given above, instead of this, it is also conceivable to cause the delay characteristics of the gain G to be variable in response to iris characteristic change with time (e.g., characteristic change associated with aging degradation of a mechanical part), for example.

In any case, it is possible to change brightness change characteristics according to electronic brightness adjustment to characteristics corresponding to brightness change characteristics according to optical brightness adjustment in response to a case in which iris characteristics change due to a certain circumstance by configuring the delay characteristics of the gain to be variable. That is, it is possible to promote mitigation of a discomfort of a user during brightness adjustment switching and curbing of deterioration in operability with respect to brightness adjustment in response to a case in which iris characteristics changes due to a certain circumstance.

[3-2. Second Modified Example]

Figure 10:
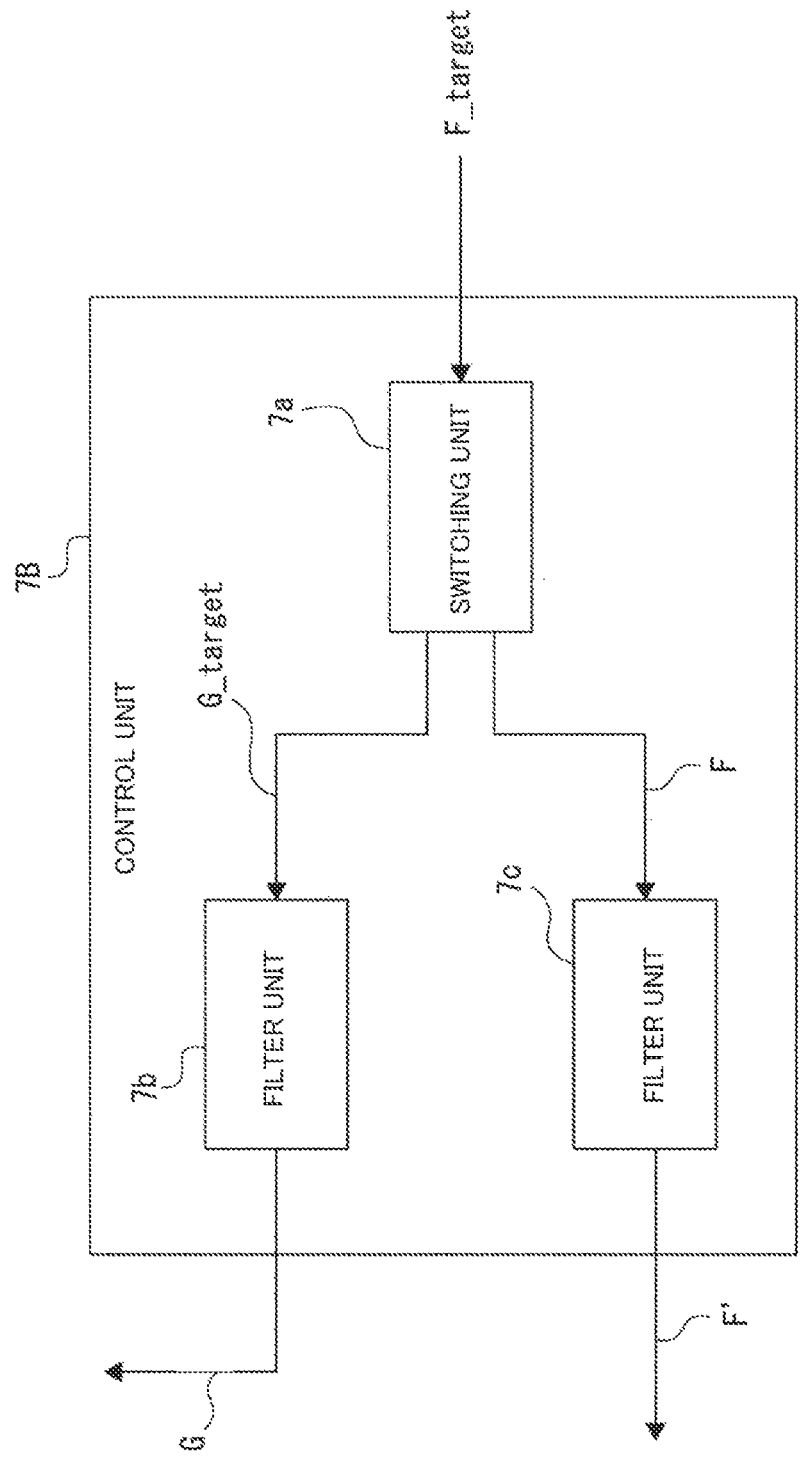
FIG. 10 is a diagram for describing a configuration of an imaging system as a second modified example.

In addition, it is also conceivable to delay not only the gain G side but also the iris side (F value side). Specifically, a filter unit 7c that delays the F value output from the switching unit 7a is provided along with the filter unit 7b that delays the target value G_target of the gain G as in a control unit 7B shown in FIG. 10. According to this configuration, change in the F value with respect to change in the target value F_target as a brightness indication value is delayed in optical brightness adjustment. Although not illustrated, the F value (represented by "F"' in the figure) that has passed through the filter unit 7c is indicated to the iris driving unit 11 in the imaging system in this case.

According to this, on the assumption that there are ideal iris response characteristics, for example, it is possible to cause total characteristics of "iris+filter" to be identical to the ideal iris response characteristics by applying a filter to the gain G such that characteristics thereof becomes identical to the ideal response characteristics and, for an iris that does not have ideal response characteristics, providing a filter before the iris.

Accordingly, the ideal response characteristics can be realized in both optical brightness adjustment and electronic brightness adjustment, and thus it is possible to promote mitigation of a discomfort of a user with respect to brightness adjustment and curbing of deterioration in operability with respect to brightness adjustment.

[3-3. Other Modified Examples]

Figure 11:
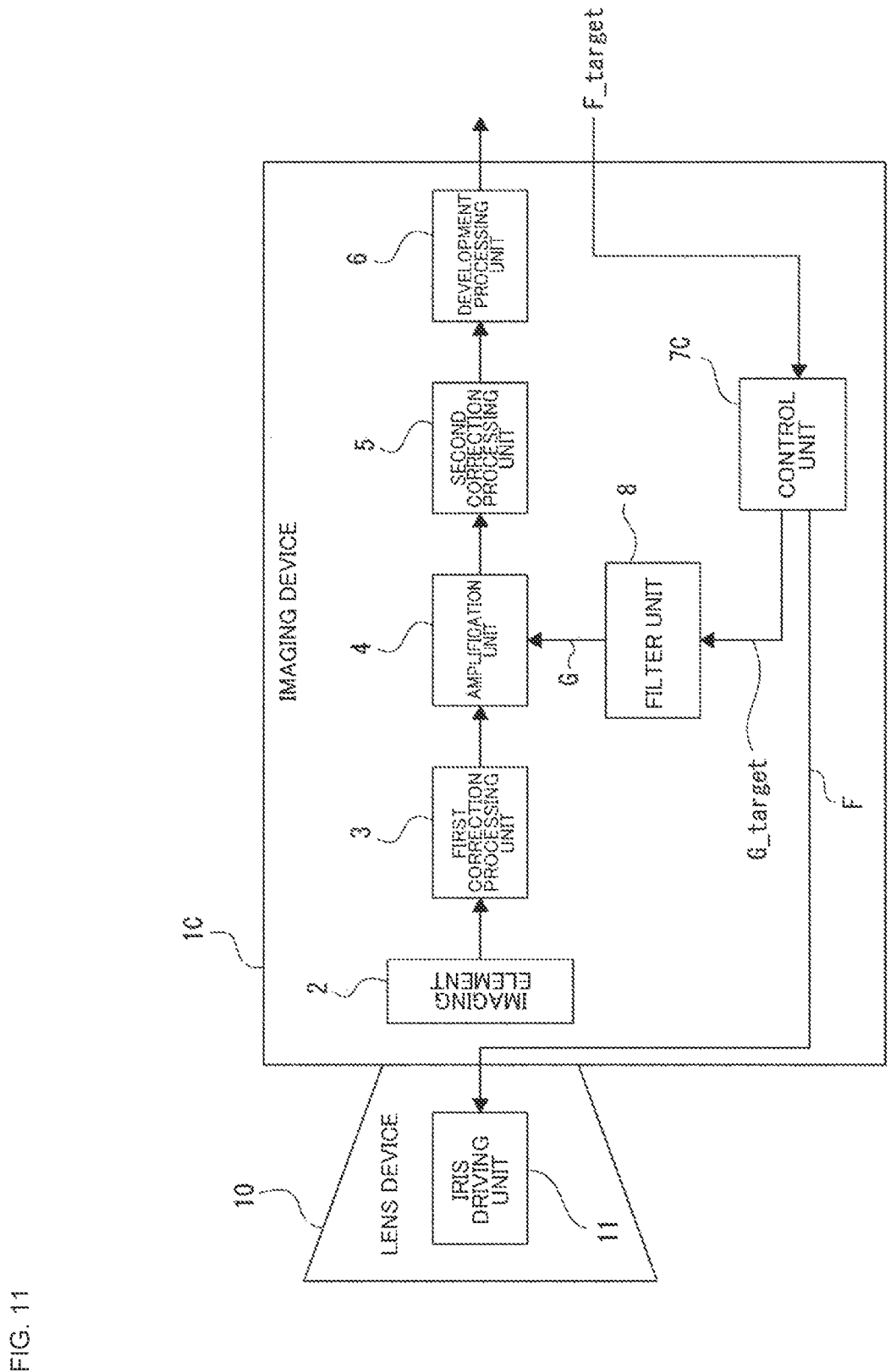
FIG. 11 is an explanatory diagram with respect to a modified example of a filter unit.

Meanwhile, although an example in which filter processing for delaying the gain G is performed as software processing of the control unit 7 has been given above, a filter unit 8 that performs the filter processing can also be provided as an external circuit as in an imaging device 1C shown in FIG. 11, for example.

Here, the control unit 7C differs from the control unit 7 in that it includes the switching unit 7a shown in FIG. 7 as a functional unit with respect to brightness adjustment and the filter unit 7b is omitted. The filter unit 8 performs filter processing for delaying change in the target value G_target output from the control unit 7 (switching unit 7a) with respect to change in the target value F_target of the F value and outputs a gain G acquired through the filter processing to the amplification unit 4.

Figure 12:
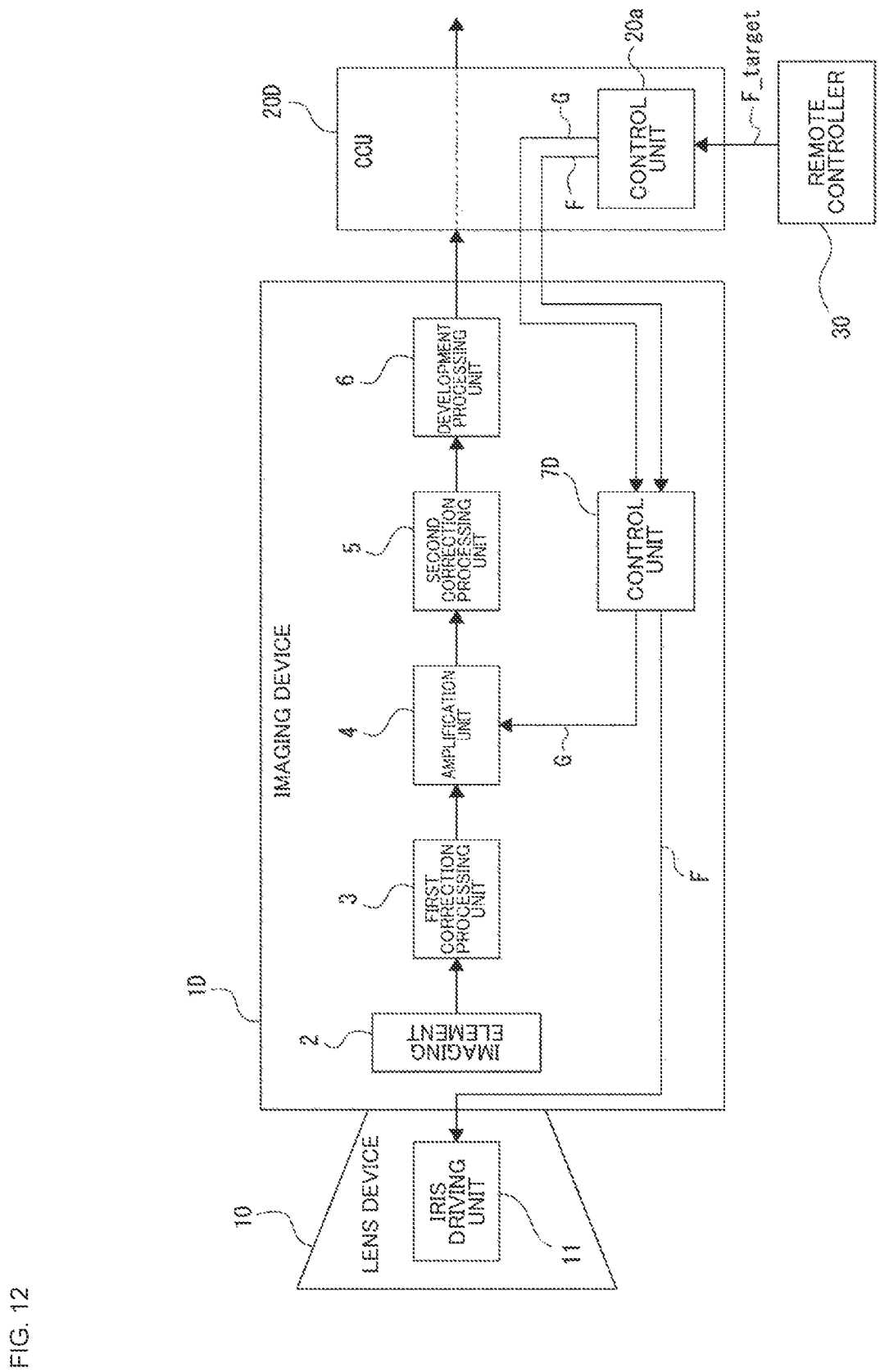
FIG. 12 is an explanatory diagram with respect to a modified example of performing control relating to brightness adjustment as an embodiment in camera control unit (CCU).

In addition, although an example in which the control unit 7 in the imaging device 1 executes control with respect to brightness adjustment as an embodiment has been given in the above description, the control can also be performed by the CCU 20. FIG. 12 shows a configuration example of the imaging system in such a case.

In the imaging system in this case, an imaging device 1D is provided instead of the imaging device 1 and a CCU 20D is provided instead of the CCU 20. The CCU 20D includes, for example, a control unit 20a composed of a microcomputer including a CPU, a ROM, a RAM, and the like. This control unit 20a performs operation control of the imaging device 1D, for example, on the basis of operation input information or the like from the remote controller 30.

Although not illustrated, functional units with respect to brightness adjustment shown in FIG. 7 are provided for the control unit 20a of the CCU 20D in the imaging system in this case. Specifically, the functional units are the switching unit 7a and the filter unit 7b.

In this case, the F value output from the switching unit 7a included in the control unit 20a and the gain G output from the filter unit 7b included in the control unit 20a are respectively indicated to the iris driving unit 11 and the amplification unit 4 via the control unit 7D included in the imaging device 1D. Meanwhile, the control unit 7D differs from the control unit 7 in that the switching unit 7a and the filter unit 7b are omitted.

4. Conclusion of Embodiments

As described above, the signal processing device (imaging device 1 or CCU 20D) of an embodiment includes a switching unit (switching unit 7a) that performs, in response to change in an indication value indicating the brightness of a captured image obtained by the imaging device, switching between optical brightness adjustment that is brightness adjustment according to an iris and electronic brightness adjustment that is brightness adjustment according to application of a gain depending on the indication value to the captured image, and a first delay unit (filter units 7b and 8) that delays change in the gain with respect to change in the indication value in the electronic brightness adjustment.

By delaying change in the gain with respect to change in the indication value in electronic brightness adjustment, a degree of change in brightness is prevented from abruptly changing even when the indication value has changed to be a threshold value or less and thus brightness adjustment has switched from optical brightness adjustment to electronic brightness adjustment.

Accordingly, it is possible to promote mitigation of a discomfort of a user or an output image observer during brightness adjustment switching and curbing of deterioration in operability with respect to brightness adjustment while promoting curbing of resolution decrease due to execution of only optical brightness adjustment.

In addition, in the signal processing device of the embodiment, the indication value is a target value F_target of an F value.

Accordingly, it is not necessary to convert a brightness indication value other than the F value into an F value in execution of optical brightness adjustment. Therefore, it is possible to promote reduction in a processing load with respect to brightness adjustment.

Further, in the signal processing device of the embodiment, the switching unit performs switching control on the basis of a result of comparison between the indication value and a threshold value.

Accordingly, optical brightness adjustment is performed having a predetermined F value as a limit.

Therefore, it is possible to improve the effect of curbing resolution decrease.

In addition, in the signal processing device of the embodiment, the indication value is a target value of an F value, and the switching unit performs switching control such that optical brightness adjustment is performed on a side on which the target value of the F value is large and electronic brightness adjustment is performed on a side on which the target value of the F value is small, with respect to the threshold value.

That is, optical brightness adjustment is performed in a region where the F value is large and resolution is high and electronic brightness adjustment instead of optical brightness adjustment is performed in a region where the F value is small and resolution tends to decrease.

Accordingly, it is possible to promote curbing of resolution decrease associated with brightness adjustment.

Furthermore, in the signal processing device of the embodiment, the first delay unit changes a gain change speed within a period (period after the point in time T1 in FIG. 8B) in which the gain is changed in electronic brightness adjustment. Accordingly, it is possible to approximate brightness change characteristics according to electronic brightness adjustment to brightness change characteristics according to optical brightness adjustment.

Therefore, seamlessness of change in brightness during brightness adjustment switching is improved, and thus it is possible to enhance the effect of mitigating a discomfort of a user or an output image observer with respect to change in brightness and the effect of curbing deterioration of operability with respect to brightness adjustment.

In addition, in the signal processing device of the embodiment, the first delay unit suppresses a gain change speed to a predetermined speed or less in electronic brightness adjustment.

There is an upper limit in a speed of change of brightness in optical brightness adjustment due to characteristics of the iris.

Accordingly, it is possible to approximate brightness change characteristics according to electronic brightness adjustment to brightness change characteristics according to optical brightness adjustment by suppressing the gain change speed to the predetermined speed or less in electronic brightness adjustment, and thus it is possible to enhance the effect of mitigating a discomfort of a user or an output image observer with respect to change in brightness and the effect of curbing deterioration of operability with respect to brightness adjustment.

Further, in the signal processing device of the embodiment, the first delay unit delays the gain according to delay characteristics imitating inertia in electronic brightness adjustment.

Accordingly, it is possible to cause brightness change characteristics according to electronic brightness adjustment to be change characteristics to which inertia acting on the iris has been added.

Therefore, it is possible to approximate brightness change characteristics according to electronic brightness adjustment to brightness change characteristics according to optical brightness adjustment, and thus it is possible to enhance the effect of mitigating a discomfort of a user or an output image observer with respect to change in brightness and the effect of curbing deterioration of operability with respect to brightness adjustment.

Furthermore, in the signal processing device of the embodiment, the switching unit is configured to be able to switch between a switching mode in which control of switching between optical brightness adjustment and electronic brightness adjustment is performed in response to change in the indication value and a non-switching mode in which switching control is not performed with respect to change in the indication value and optical brightness adjustment is executed.

Accordingly, the F value can be decreased to a minimum value.

Therefore, it is possible to promote efficiency of a flange back adjustment work. Further, it is possible to promote response to intention to create an image such as intention to generate background blur.

In addition, in the signal processing device of the embodiment, the switching unit performs switching between the switching mode and the non-switching mode on the basis of an operation.

Accordingly, it is possible to perform switching between the switching mode and the non-switching mode on the basis of an intention of a user.

Therefore, it is possible to promote improvement of convenience of the user.

Further, in the signal processing device of the embodiment, the switching unit performs switching between the switching mode and the non-switching mode on the basis of an operation of the remote controller (remote controller 30).

Accordingly, a burden of operation of switching between the switching mode and the non-switching mode is not imposed on a cameraman.

Since flange back adjustment is performed by the cameraman, it is not desirable to impose an extra operation burden on the cameraman during flange back adjustment in terms of efficiency of an adjustment work. If mode switching is performed on the basis of the operation of the remote controller as described above, a person other than the cameraman such as a video engineer can be caused to perform the mode switching operation and thus it is possible to promote reduction in an operation burden of the cameraman during flange back adjustment to promote efficiency of the adjustment work.

Furthermore, in the signal processing device of the embodiment, the first delay unit is configured to be able to change delay characteristics of the gain in electronic brightness adjustment.

Accordingly, it is possible to change brightness change characteristics according to electronic brightness adjustment to characteristics corresponding to brightness change characteristics according to optical brightness adjustment in response to a case in which iris characteristics change due to a certain circumstance.

That is, it is possible to promote mitigation of a discomfort of a user or an output image observer during brightness adjustment switching and curbing of deterioration in operability with respect to brightness adjustment in response to a case in which iris characteristics change due to a certain circumstance.

In addition, in the signal processing device of the embodiment, the imaging device is a lens interchangeable type imaging device, and the first delay unit delays change in the gain according to delay characteristics based on information acquired from a lens device mounted in the imaging device.

Accordingly, it is possible to cause change characteristics of brightness according to electronic brightness adjustment to be characteristics suitable for a lens device in response to a case in which iris characteristics vary according to lens devices to be mounted.

That is, it is possible to promote mitigation of a discomfort of a user or an output image observer during brightness adjustment switching and curbing of deterioration in operability with respect to brightness adjustment in response to a case in which iris characteristics vary according to lens devices to be mounted.

Further, the signal processing device of the embodiment includes a second delay unit (filter unit 7c) that delays change in the F value with respect to change in the indication value in optical brightness adjustment.

Accordingly, it is possible to cause change characteristics of the F value with respect to change in the indication value to be desired characteristics.

Therefore, it is possible to promote mitigation of a discomfort of a user or an output image observer with respect to brightness adjustment and curbing of deterioration in operability with respect to brightness adjustment.

In addition, an imaging device (imaging devices 1, 1A, 1C, and 1D) of the embodiment includes an imaging element (imaging element 2) that receives incident light through an iris to acquire a captured image, a switching unit (switching unit 7a) that performs, in response to change in an indication value indicating brightness of the captured image, switching between optical brightness adjustment that is brightness adjustment according to the iris and electronic brightness adjustment that is brightness adjustment according to application of a gain depending on an indication value to the captured image, and a first delay unit (filter units 7b and 8) that delays change in the gain with respect to change in the indication value in electronic brightness adjustment.

According to the imaging device according to this embodiment, it is possible to obtain similar operation and effects as those of the signal processing device according to the foregoing embodiment.

5. Application Examples

The technology according to the present disclosure can be applied to various products. For example, the technology according to the present disclosure may be applied to an operating room system.

Figure 13:
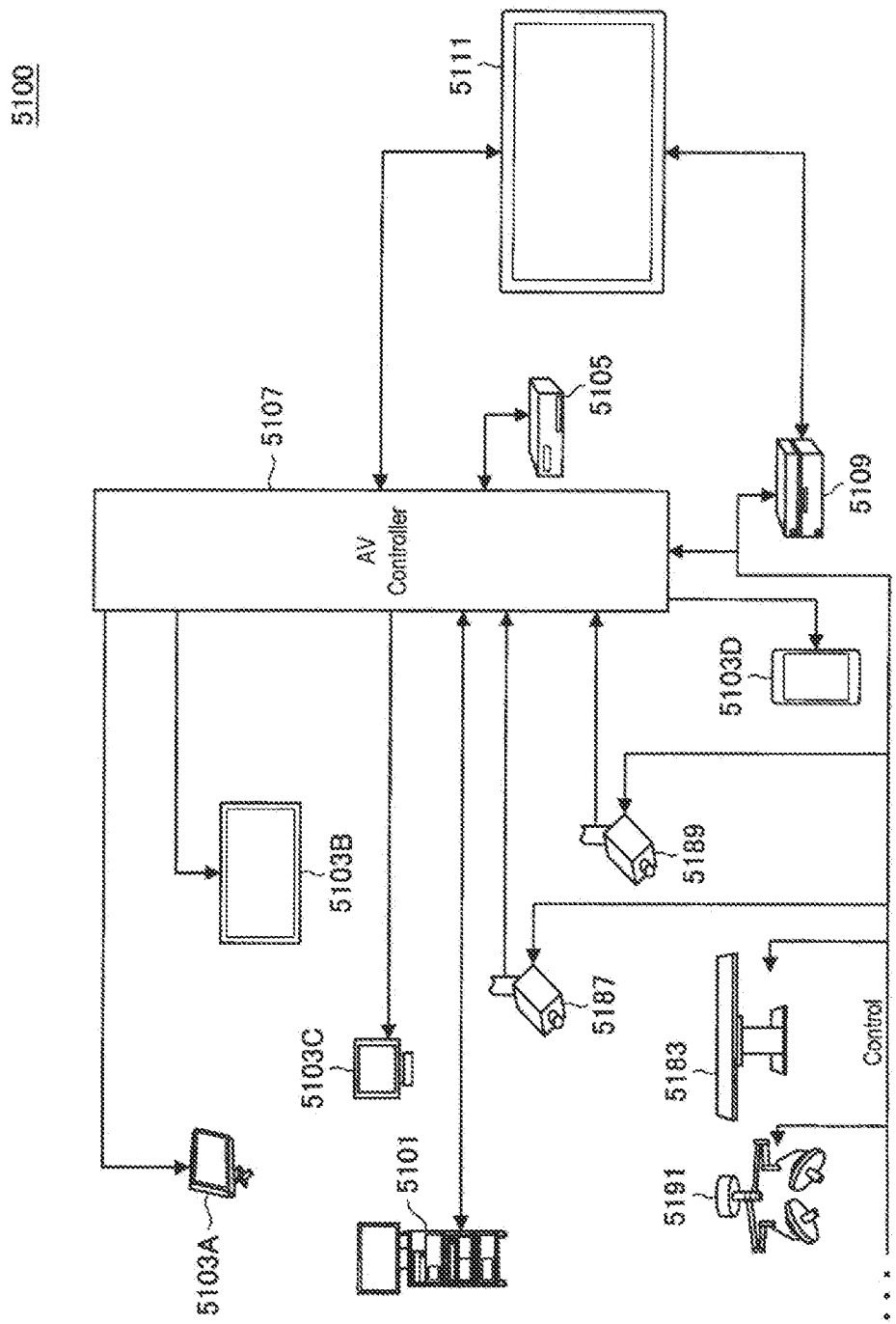
FIG. 13 is a diagram schematically illustrating an overall configuration of an operating room system.

FIG. 13 is a diagram schematically illustrating an overall configuration of an operating room system 5100 to which the technology according to the present disclosure is applied. Referring to FIG. 13, the operating room system 5100 is configured by connecting a group of devices provided in an operating room in a coordinated manner via an audiovisual controller (AV Controller) 5107 and an operating room control device 5109.

Various devices can be installed in the operating room. In FIG. 13, as an example, various device groups 5101 for endoscopic surgery, a ceiling camera 5187 provided on a ceiling of the operating room to image hands of a surgeon, an operating room camera 5189 provided on the ceiling of the operating room to image a state of the entire operating room, a plurality of display devices 5103A to 5103D, a recorder 5105, a patient bed 5183, and lighting 5191 are illustrated.

Here, among these devices, the device groups 5101 belong to an endoscopic surgery system 5113, which will be described later, and include an endoscope, a display device that displays an image captured by the endoscope, and the like. Each device belonging to the endoscopic surgery system 5113 is also referred to as a medical device. On the other hand, the display devices 5103A to 5103D, the recorder 5105, the patient bed 5183, and the lighting 5191 are devices provided in the operating room, for example, separately from the endoscopic surgery system 5113. Each device that does not belong to the endoscopic surgery system 5113 is also referred to as a non-medical device. The audiovisual controller 5107 and/or the operating room control device 5109 controls operations of these medical devices and non-medical devices in cooperation with each other.

The audiovisual controller 5107 controls overall processing related to image display in the medical devices and non-medical devices. Specifically, among the devices included in the operating room system 5100, the device groups 5101, the ceiling camera 5187, and the operating room camera 5189 may be devices (hereinafter, also referred to as source devices) having a function of transmitting information to be displayed during surgery (hereinafter, also referred to as display information). Further, the display devices 5103A to 5103D may be devices for outputting the display information (hereinafter, also referred to as output destination devices). In addition, the recorder 5105 may be a device that belongs to both the source devices and the output destination devices. The audiovisual controller 5107 has a function of controlling operations of the source devices and the output destination devices, acquiring the display information from the source devices, and transmitting the display information to cause the output destination devices to display or record it. Also, the display information includes various images captured during surgery, various information related to surgery (for example, physical information of a patient, test results in the past, information on a surgical procedure, etc.), and the like.

Specifically, as the display information, information about images of a surgical part in the patient's body cavity captured by the endoscope may be transmitted from the device groups 5101 to the audiovisual controller 5107. Also, as the display information, information about images in the vicinity of the operator captured by the ceiling camera 5187 may be transmitted from the ceiling camera 5187. Also, as display information, information about images showing a state of the entire operating room captured by the operating room camera 5189 may be transmitted from the operating room camera 5189. In a case in which the operating room system 5100 has another device having an imaging function, the audiovisual controller 5107 may also acquire information about images captured by the other device from the other device as the display information.

Alternatively, for example, the information about these images captured in the past is recorded in the recorder 5105 by the audiovisual controller 5107. The audiovisual controller 5107 can acquire the information about the images captured in the past from the recorder 5105 as the display information. Also, various information about surgery may be recorded in advance in the recorder 5105.

The audiovisual controller 5107 causes at least one of the display devices 5103A to 5103D, which are the output destination devices, to display the acquired display information (that is, the images captured during surgery and various information about surgery). In the illustrated example, the display device 5103A is a display device suspended from and installed at the ceiling of the operating room, the display device 5103B is a display device installed on a wall surface of the operating room, the display device 5103C is a display device installed on a desk in the operating room, and the display device 5103D is a mobile device having a display function (for example, a tablet personal computer (PC)).

Further, although not illustrated in FIG. 13, the operating room system 5100 may include devices outside the operating room. The devices outside the operating room may be, for example, a server connected to a network constructed inside or outside a hospital, a PC used by medical staff, and a projector installed in a conference room of the hospital. When such an external device is outside the hospital, the audiovisual controller 5107 can also display the display information on a display device of another hospital via a video conferencing system or the like for telemedicine.

The operating room control device 5109 controls overall processing other than the processing related to image display in the non-medical devices. For example, the operating room control device 5109 controls driving of the patient bed 5183, the ceiling camera 5187, the operating room camera 5189, and the lighting 5191.

The operating room system 5100 is provided with a centralized operation panel 5111, and a user can give an instruction about image display to the audiovisual controller 5107 and an instruction about operations of the non-medical devices to the operating room control device 5109 via the centralized operation panel 5111. The centralized operation panel 5111 is configured by providing a touch panel on a display surface of a display device.

Figure 14:
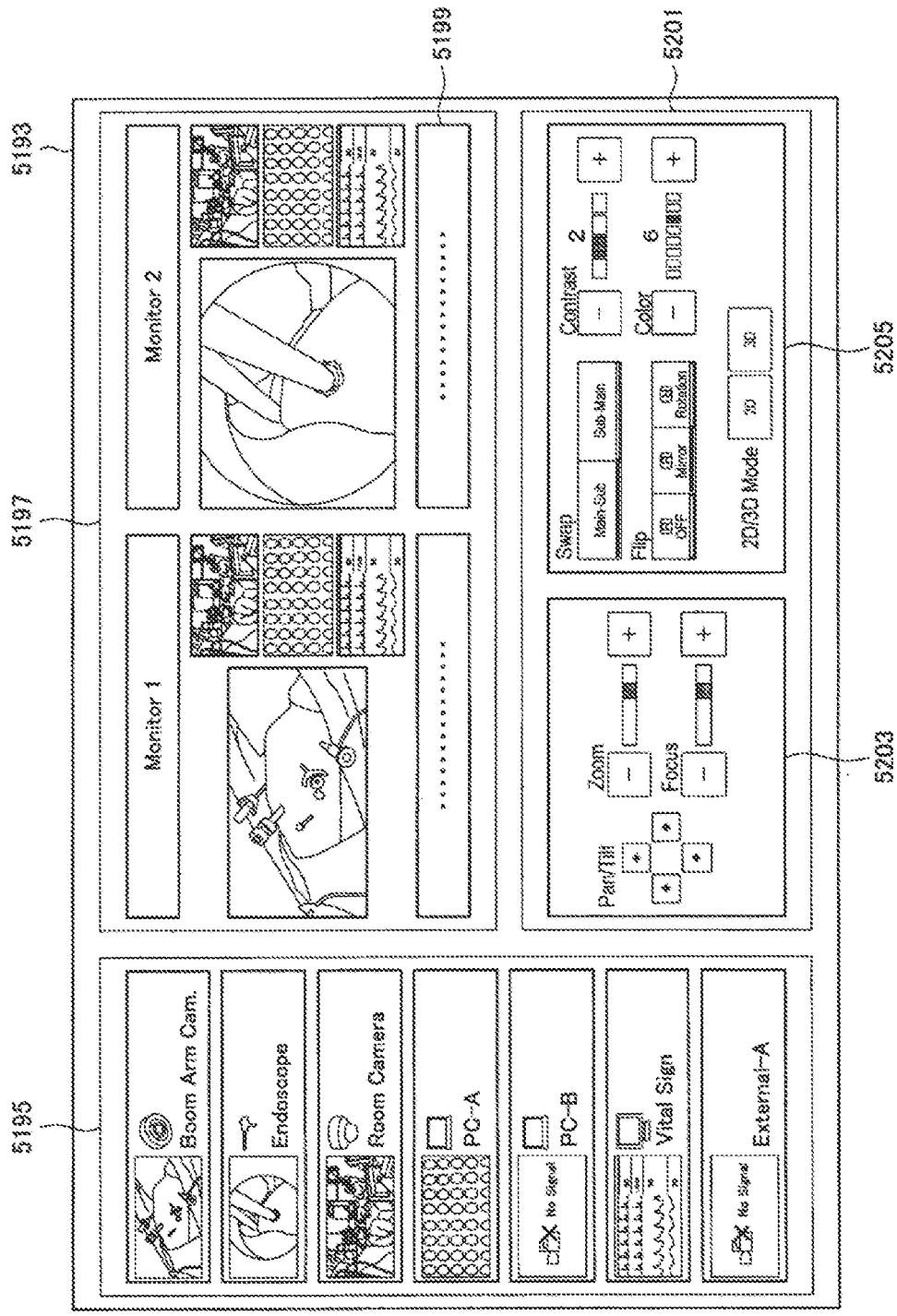
FIG. 14 is a diagram illustrating a display example of an operation screen in a centralized operation panel.

FIG. 14 is a diagram illustrating a display example of an operation screen in the centralized operation panel 5111. In FIG. 14, as an example, an operation screen corresponding to a case in which the operating room system 5100 is provided with two display devices as output destination devices is shown. Referring to FIG. 14, the operation screen 5193 is provided with a source selection area 5195, a preview area 5197, and a control area 5201.

In the source selection area 5195, the source devices provided in the operating room system 5100 and thumbnail screens showing the display information held by the source devices are linked and displayed. The user can select the display information to be displayed on a display device from any of the source devices displayed in the source selection area 5195.

In the preview area 5197, previews of screens displayed on the two display devices (Monitor 1 and Monitor 2), which are the output destination devices, are displayed. In the illustrated example, four images are P in P displayed on one display device. The four images correspond to the display information transmitted from the source devices selected in the source selection area 5195. Among the four images, one is displayed relatively large as a main image and the remaining three are displayed relatively small as sub-images. The user can switch the main image and the sub images by appropriately selecting an area in which the four images are displayed. Further, a status display area 5199 is provided below the area in which the four images are displayed, and status related to surgery (for example, elapsed time of surgery, physical information of the patient, etc.) may be appropriately displayed in the area.

The control area 5201 is provided with a source operation area 5203 in which graphical user interface (GUI) components for operating the source devices are displayed and an output destination operation area 5205 in which the GUI components for performing operations on the output destination devices are displayed. In the illustrated example, the source operation area 5203 is provided with the GUI components for performing various operations (pan, tilt, and zoom) on cameras in the source devices having an imaging function. The user can operate operations of the cameras in the source devices by appropriately selecting these GUI components. Also, although not shown, in a case in which the source device selected in the source selection area 5195 is the recorder (that is, in a case in which an image recorded in the recorder in the past is displayed in the preview area 5197), the source operation area 5203 may be provided with GUI components for performing operations such as playing, stopping, rewinding, and fast-forwarding the image.

Further, the output destination operation area 5205 is provided with GUI components for performing various display operations (swap, flip, color adjustment, contrast adjustment, and switching between 2D display and 3D display) on display devices that are the output destination devices. The user can operate the display on the display devices by appropriately selecting these GUI components.

Also, the operation screens displayed on the centralized operation panel 5111 are not limited to the illustrated example, and the user may be able to input operations to each device provided in the operating room system 5100, which can be controlled by the audiovisual controller 5107 and the operating room control device 5109, through the centralized operation panel 5111.

Figure 15:
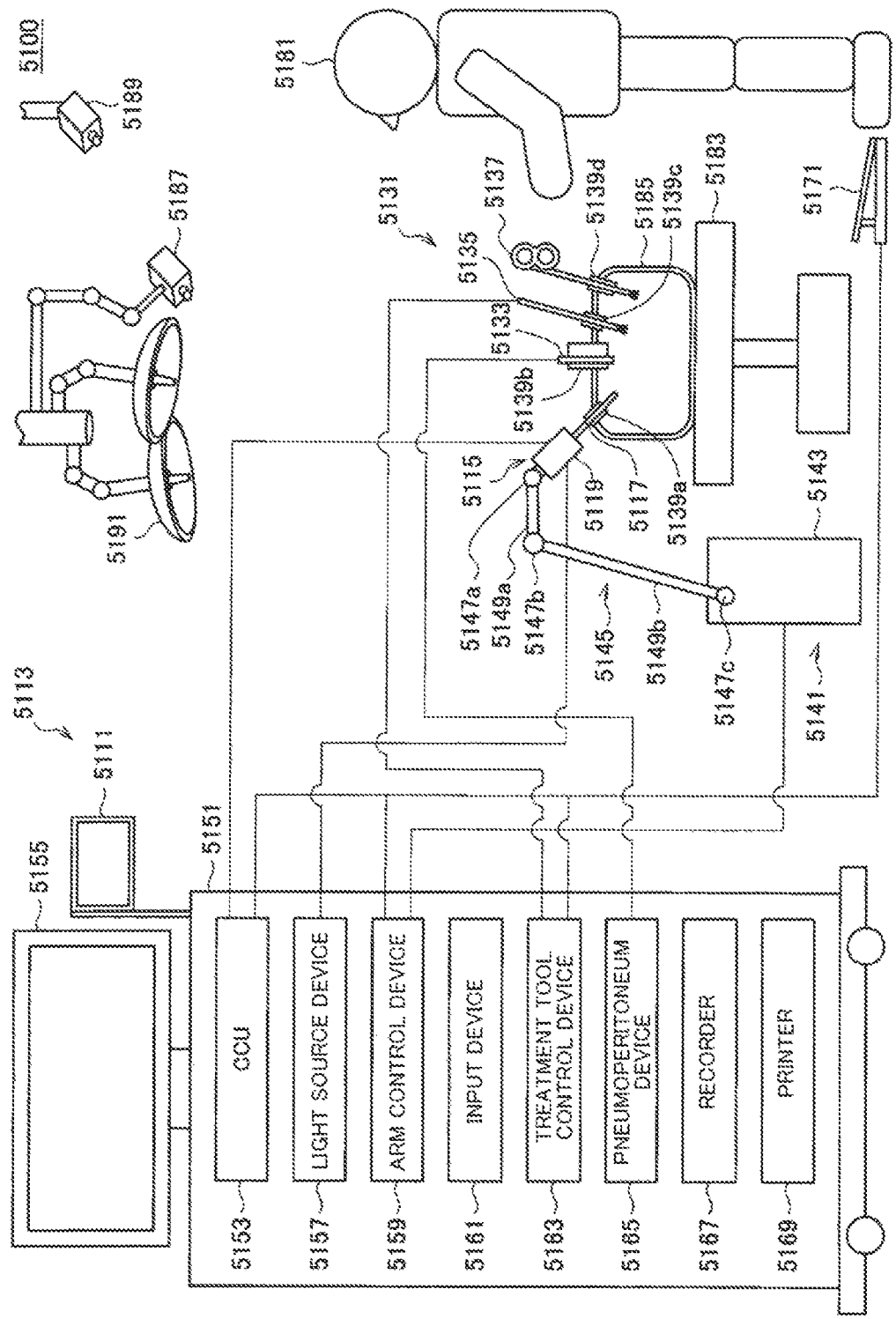
FIG. 15 is a diagram illustrating an example of a state of an operation to which an operating room system is applied.

FIG. 15 is a diagram illustrating an example of a state of the surgery in which the operating room system described above is applied. The ceiling camera 5187 and the operating room camera 5189 are provided on the ceiling of the operating room, and can image hands of a surgeon (doctor) 5181 who treats an affected part of a patient 5185 on the patient bed 5183 and a state of the entire operating room. The ceiling camera 5187 and the operating room camera 5189 may be provided with a magnification adjustment function, a focal length adjustment function, an imaging direction adjustment function, and the like. The lighting 5191 is provided on the ceiling of the operating room and irradiates at least the hands of the surgeon 5181. In the lighting 5191, an amount of irradiation light, a wavelength (color) of the irradiation light, an irradiation direction of the light, and the like may be appropriately adjusted.

The endoscopic surgery system 5113, the patient bed 5183, the ceiling camera 5187, the operating room camera 5189, and the lighting 5191 are connected so that these can cooperate with each other via the audiovisual controller 5107 and the operating room control device 5109 (not illustrated in FIG. 15), as illustrated in FIG. 13. The centralized operation panel 5111 is provided in the operating room, and the user can appropriately operate these devices present in the operating room through the centralized operation panel 5111, as described above.

Hereinafter, a configuration of the endoscopic surgery system 5113 will be described in detail. As shown in the drawing, the endoscopic surgery system 5113 includes an endoscope 5115, other surgical instruments 5131, a supporting arm device 5141 that supports the endoscope 5115, and a cart 5151 on which various devices for an endoscopic surgical operation are mounted.

In the endoscopic surgery, instead of cutting an abdominal wall to open the abdomen, a plurality of tubular laparotomy devices called trocars 5139a to 5139d are punctured into the abdominal wall. Then, from the trocars 5139a to 5139d, a lens-barrel 5117 of the endoscope 5115 and other surgical tools 5131 are inserted into the body cavity of the patient 5185. In the illustrated example, as other surgical tools 5131, a pneumoperitoneum tube 5133, an energy treatment tool 5135, and forceps 5137 are inserted into the body cavity of patient 5185. Further, the energy treatment tool 5135 is a treatment tool that cuts and peels tissue, seals a blood vessel, or the like by using a high-frequency current or ultrasonic vibration. However, the illustrated surgical tools 5131 are merely exemplary, and as the surgical tools 5131, various surgical tools generally used in the endoscopic surgery such as a tweezer and a retractor may be used.

An image of a surgical part within the body cavity of the patient 5185 imaged by the endoscope 5115 is displayed on a display device 5155. The surgeon 5181 performs treatment such as cutting-out of an affected part, using the energy treatment tool 5135 or the forceps 5137 while viewing the image of the surgical part displayed on the display device 5155 in real time. Meanwhile, although not shown in the drawing, the pneumoperitoneum tube 5133, the energy treatment tool 5135, and the forceps 5137 are supported by the surgeon 5181, an assistant, or the like during a surgical operation.

(Supporting Arm Device)

The supporting arm device 5141 includes an arm portion 5145 extending from a base portion 5143. In the example shown in the drawing, the arm portion 5145 includes joint portions 5147a, 5147b, and 5147c and links 5149a and 5149b, and is driven under the control of an arm control device 5159. The endoscope 5115 is supported by the arm portion 5145, and the position and posture thereof are controlled. Thereby, fixation of the stable position of the endoscope 5115 can be realized.

(Endoscope)

The endoscope 5115 includes the lens-barrel 5117 configured such that a region having a predetermined length from a tip end thereof is inserted into the body cavity of the patient 5185, and a camera head 5119 connected to a base end of the lens-barrel 5117. In the example shown in the drawing, the endoscope 5115 configured as a so-called hard mirror including a hard lens-barrel 5117 is shown, but the endoscope 5115 may be configured as a so-called soft mirror including a soft lens-barrel 5117.

An opening in which an objective lens is fitted is provided at a tip of the lens-barrel 5117. A light source device 5157 is connected to the endoscope 5115, and light generated by the light source device 5157 is guided to the tip of the lens-barrel by a light guide extending inside the lens-barrel 5117, and is radiated toward an observation target in the body cavity of the patient 5185 through the objective lens. The endoscope 5115 may be a direct endoscope, a perspective endoscope, or a side endoscope.

An optical system and an imaging element are provided inside the camera head 5119, and reflected light (observation light) from the observation target is condensed on the imaging element by the optical system. The observation light is subjected to photoelectric conversion by the imaging element, and an electrical signal corresponding to the observation light, that is, an image signal corresponding to an observation image is generated. The image signal is transmitted to a camera control unit (CCU) 5153 as RAW data. Meanwhile, the camera head 5119 is equipped with a function of adjusting magnification and a focal length by appropriately driving the optical system.

Meanwhile, for example, in order to cope with stereoscopic vision (3D display) and the like, the camera head 5119 may be provided with a plurality of imaging elements. In this case, a plurality of relay optical systems are provided inside the lens-barrel 5117 in order to guide observation light to each of the plurality of imaging elements.

(Various Devices Mounted on Cart)

The CCU 5153 includes, for example, a central processing unit (CPU) and a graphics processing unit (GPU), and generally controls operations of the endoscope 5115 and the display device 5155. Specifically, the CCU 5153 performs various image processing for displaying an image based on an image signal, such as development processing (demosaic processing), on the image signal received from the camera head 5119. The CCU 5153 provides the image signal subjected to the image processing to the display device 5155. In addition, the audiovisual controller 5107 shown in FIG. 13 is connected to the CCU 5153. The CCU 5153 also provides the image signal subjected to the image processing to the audiovisual controller 5107. Further, the CCU 5153 transmits a control signal to the camera head 5119 and controls drive thereof. The control signal may include information about imaging conditions such as a magnification and a focal length. The information regarding the imaging conditions may be input via an input device 5161 or may be input via the centralized operation panel 5111 described above.

The display device 5155 displays an image based on an image signal having been subjected to image processing by the CCU 5153 under the control of the CCU 5153. In a case where the endoscope 5115 is an endoscope dealing with high-resolution imaging such as 4K (the number of horizontal pixels 3840×the number of vertical pixels 2160) or 8K (the number of horizontal pixels 7680×the number of vertical pixels 4320) and/or is an endoscope dealing with 3D display, a display device capable of performing high-resolution display and/or 3D display may be used for the respective endoscopes as the display device 5155. In a case where the endoscope 5115 is an endoscope dealing with high-resolution imaging such as 4K or 8K, a further immersive feeling can be obtained by using a display device having a size of 55 inches or more as the display device 5155. In addition, a plurality of display devices 5155 having different resolutions and sizes may be provided depending on the application thereof.

The light source device 5157 is configured of a light source such as a light emitting diode (LED) and supplies the endoscope 5115 with irradiation light for imaging the surgical part or the like.

The arm control device 5159 is constituted by a processor such as a CPU and operates in accordance with a predetermined program to control the driving of the arm portion 5145 of the supporting arm device 5141 in accordance with a predetermined control method.

The input device 5161 is an input interface for the endoscopic surgery system 5113. A user can input various information and an instruction to the endoscopic surgery system 5113 through the input device 5161. For example, the user inputs various information on a surgical operation, such as body information of a patient or information on an operative method of the surgical operation, through the input device 5161. In addition, for example, the user inputs an instruction indicating that the arm portion 5145 is driven, an instruction indicating that imaging conditions of the endoscope 5115 (the type of irradiation light, magnification, a focal distance, and the like) are changed, an instruction indicating that the energy treatment tool 5135 is driven, or the like through the input device 5161.

The type of input device 5161 is not limited, and the input device 5161 may be various known input devices. As the input device 5161, for example, a mouse, a keyboard, a touch panel, a switch, a foot switch 5171, a lever, and/or the like can be applied. In a case where a touch panel is used as the input device 5161, the touch panel may be provided on a display surface of the display device 5155.

Alternatively, the input device 5161 is a device put on the user, such as a glasses-type wearable device or a head mounted display (HMD), and various inputs are performed in accordance with the user's gesture and line of sight detected by these devices. Further, the input device 5161 includes a camera capable of detecting movement of the user, and various inputs are performed in accordance with the user's gesture and line of sight detected from images captured by the camera. Further, the input device 5161 includes a microphone capable of picking up the user's voice, and various inputs are performed by means of voice through the microphone. In this way, the input device 5161 is configured to be able to input various information in a non-contact manner, so that the user particularly in a clean area (for example, the surgeon 5181) can operate a device in a dirty area in a non-contact manner. In addition, the user can operate the device without taking his/her hand off the surgical tools that he/she has, which improves the convenience for the user.

A treatment tool control device 5163 controls driving of the energy treatment tool 5135 for cauterizing or incising tissue, sealing a blood vessel, or the like. A pneumoperitoneum device 5165 sends a gas into the body cavity through the pneumoperitoneum tube 5133 in order to inflate the body cavity of the patient 5185 for the purpose of securing a visual field for the endoscope 5115 and a working space for the operator. A recorder 5167 is a device capable of recording various information about surgery. A printer 5169 is a device capable of printing various information about surgery in various formats such as text, images, and graphs.

Hereinafter, particularly characteristic configurations in the endoscopic surgery system 5113 will be described in more detail.

(Supporting Arm Device)

The supporting arm device 5141 includes the base portion 5143 which is a base, and the arm portion 5145 extending from the base portion 5143. In the example shown in the drawing, the arm portion 5145 includes the plurality of joint portions 5147a, 5147b, and 5147c and the plurality of links 5149a and 5149b connected to each other by the joint portion 5147b, but the configuration of the arm portion 5145 is simply shown in FIG. 15 for the purpose of simplification. Actually, the shapes, number, and arrangement of the joint portions 5147a to 5147c and the links 5149a and 5149b, the directions of rotation axes of the joint portions 5147a to 5147c, and the like can be appropriately set so that the arm portion 5145 has a desired degree of freedom. For example, the arm portion 5145 can be configured to preferably have a degree of freedom of 6 or more degrees of freedom. Thereby, the endoscope 5115 can be freely moved within a movable range of the arm portion 5145, and thus it is possible to insert the lens-barrel 5117 of the endoscope 5115 into the body cavity of the patient 5185 from a desired direction.

Actuators are provided at the joint portions 5147a to 5147c, and the joint portions 5147a to 5147c are configured to be rotatable around predetermined rotation axes by driving the actuators. By controlling driving of the actuators using the arm control device 5159, the rotation angles of the joint portions 5147a to 5147c are controlled, and driving of the arm portion 5145 is controlled. As a result, control of the position and the posture of the endoscope 5115 can be realized. In this case, the arm control device 5159 can control the driving of the arm portion 5145 using various known control methods such as force control or position control.

For example, the surgeon 5181 appropriately performs an operation input through the input device 5161 (including the foot switch 5171), whereby the driving of the arm portion 5145 may be appropriately controlled by the arm control device 5159 in response to the operation input, and the position and posture of the endoscope 5115 may be controlled. By the control, the endoscope 5115 which is a tip end of the arm portion 5145 can be moved from any position to any position and then fixedly supported at a position after the movement. Meanwhile, the arm portion 5145 may be operated by a so-called master slave method. In this case, the arm portion 5145 can be remotely operated by a user through the input device 5161 installed at a location separated from a surgical operating room.

Further, in a case where force control is applied, the arm control device 5159 may perform so-called power assist control for receiving an external force from a user and driving the actuators of the joint portions 5147a to 5147c so that the arm portion 5145 moves smoothly according to the external force. Thereby, when the user moves the arm portion 5145 while directly touching the arm portion 5145, the user can move the arm portion 5145 with a relatively small force. Thus, it is possible to more intuitively move the endoscope 5115 with a simpler operation and improve the convenience of the user.

Here, in general, in an endoscopic surgical operation, the endoscope 5115 is supported by a doctor called a scopist. On the other hand, the position of the endoscope 5115 can be fixed more reliably without depending on manpower by using the supporting arm device 5141, and thus it is possible to stably obtain an image of a surgical part and smoothly perform a surgical operation.

Meanwhile, the arm control device 5159 may not be necessarily provided in the cart 5151. In addition, the arm control device 5159 may not necessarily be one device. For example, the arm control device 5159 may be provided in each of the joint portions 5147a to 5147c of the arm portion 5145 of the supporting arm device 5141, and the driving control of the arm portion 5145 may be realized by a plurality of arm control devices 5159 cooperating with each other.

(Light Source Device)

The light source device 5157 supplies irradiation light at the time of imaging a surgical part to the endoscope 5115. The light source device 5157 is configured of, for example, an LED, a laser light source, or a white light source configured of a combination thereof. At this time, in a case where a white light source is constituted by a combination of RGB laser light sources, the intensity and timing of output of each color (each wavelength) can be controlled with high accuracy, and thus it is possible to adjust white balance of a captured image in the light source device 5157. Further, in this case, an object to be observed is irradiated with a laser beam emitted from each of the RGB laser light sources in a time-division manner, and the driving of an imaging element of the camera head 5119 is controlled in synchronization with an irradiation timing thereof, whereby it is also possible to capture images corresponding to RGB in a time-division manner. According to the method, it is possible to obtain a color image without providing a color filter in the imaging element.

In addition, the driving of the light source device 5157 may be controlled so as to change the intensity of output light at predetermined time intervals. The driving of the imaging element of the camera head 5119 is controlled in synchronization of a timing of the change of the light intensity to acquire images in a time-division manner, and the images are composed, whereby it is possible to generate an image having a high dynamic range without so-called blackout and overexposure.

Further, the light source device 5157 may be configured to be able to supply light in a predetermined wavelength band corresponding to special light observation. In the special light observation, for example, so-called narrow band imaging for imaging predetermined tissue such as blood vessels in the surface of the mucosa with high contrast by emitting light of a narrow band as compared with irradiation light at the time of normal observation (that is, white light) by using wavelength dependency of light absorption in body tissue is performed. Alternatively, in the special light observation, fluorescence observation for obtaining an image using fluorescence generated by emitting excitation light may be performed. In the fluorescence observation, body tissue may be irradiated with excitation light to observe fluorescence from the body tissue (autofluorescence observation), or a reagent such as indocyanine green (ICG) may be locally injected into the body tissue, and the body tissue may be irradiated with excitation light corresponding to a fluorescence wavelength of the reagent to obtain a fluorescence image. The light source device 5157 can be configured to be able to supply narrow band light and/or excitation light corresponding to such special light observation.

(Camera Head and CCU)

Figure 16:
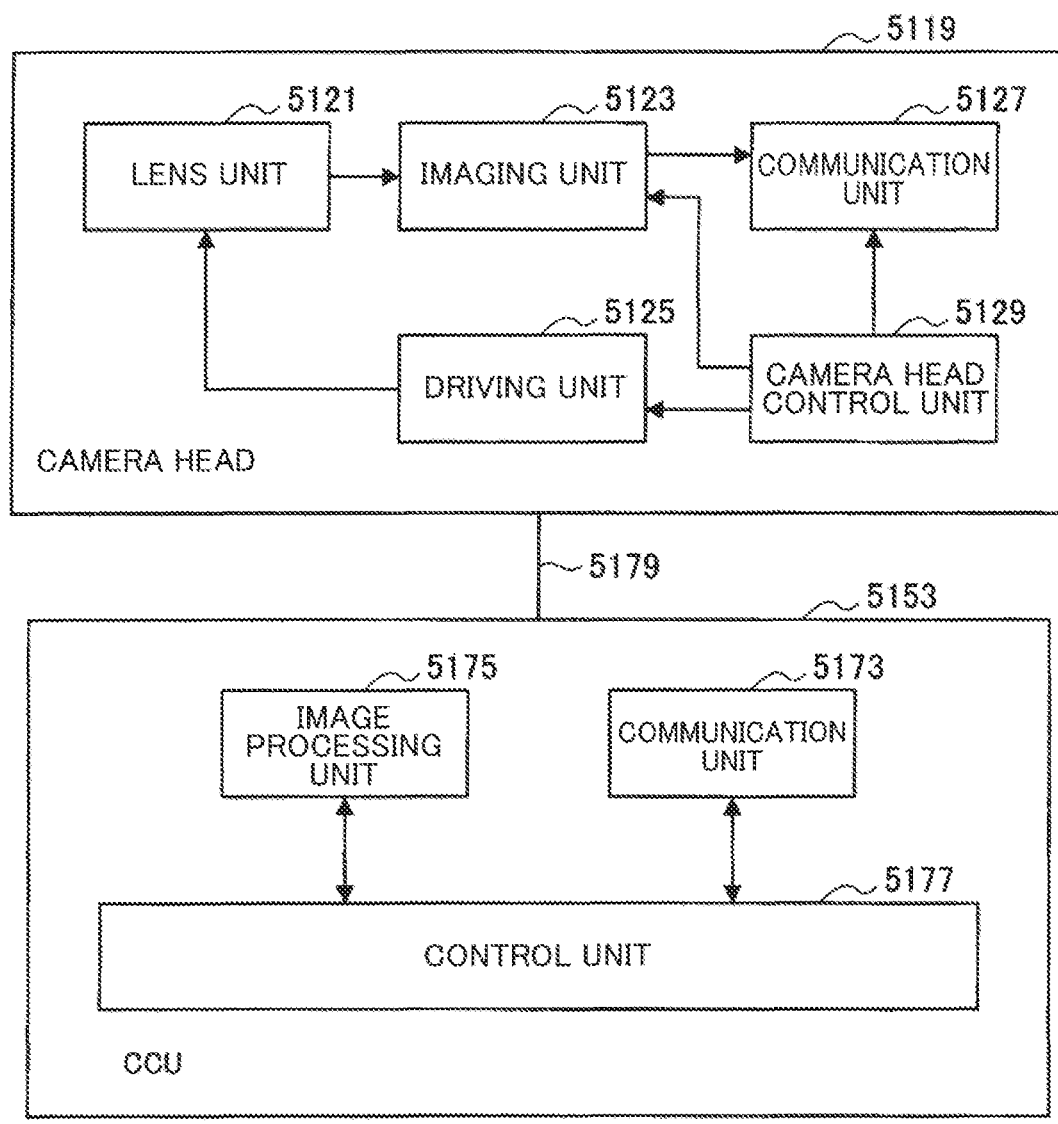
FIG. 16 is a block diagram illustrating an example of a functional configuration of a camera head and a CCU illustrated in FIG. 15.

Functions of the camera head 5119 of the endoscope 5115 and the CCU 5153 will be described in more detail with reference to FIG. 16. FIG. 16 is a block diagram showing an example of functional configurations of the camera head 5119 and the CCU 5153 shown in FIG. 15.

Referring to FIG. 16, the camera head 5119 includes a lens unit 5121, an imaging unit 5123, a driving unit 5125, a communication unit 5127, and a camera head control unit 5129 as the functions thereof. In addition, the CCU 5153 includes a communication unit 5173, an image processing unit 5175, and a control unit 5177 as the functions thereof. The camera head 5119 and the CCU 5153 are connected to each other by a transmission cable 5179 so as to be able to bidirectionally communicate with each other.

First, a functional configuration of the camera head 5119 will be described. The lens unit 5121 is an optical system provided in a connection portion with respect to the lens-barrel 5117. Observation light taken in from the top end of the lens-barrel 5117 is guided to the camera head 5119 and is incident on the lens unit 5121. The lens unit 5121 is constituted by a combination of a plurality of lenses including a zoom lens and a focus lens. Optical characteristics of the lens unit 5121 are adjusted so that observation light is condensed on a light receiving surface of an imaging element of the imaging unit 5123. In addition, the zoom lens and the focus lens are configured such that the positions thereof on the optical axes are movable in order to adjust the magnification and focus of a captured image.

The imaging unit 5123 is constituted by an imaging element and is disposed at a stage after the lens unit 5121. Observation light having passed through the lens unit 5121 is condensed on the light receiving surface of the imaging element, and an image signal corresponding to an observation image is generated by photoelectric conversion. The image signal generated by the imaging unit 5123 is provided to the communication unit 5127.

For the imaging element constituting the imaging unit 5123, for example, a complementary metal oxide semiconductor (CMOS) type image sensor having a Bayer array and capable of color photographing can be used. Also, for the imaging element, for example, an imaging element capable of photographing a high-resolution image of 4K or higher may be used. By obtaining the image of the surgical part with high resolution, the surgeon 5181 can ascertain the state of the surgical part in more detail, and surgery can proceed more smoothly.

In addition, the imaging element constituting the imaging unit 5123 is configured to include a pair of imaging elements for acquiring an image signal for a right eye and an image signal for a left eye corresponding to 3D display. By the execution of the 3D display, the surgeon 5181 can more accurately ascertain the depth of biological tissue in the surgical part. Meanwhile, in a case where the imaging unit 5123 is configured as a multi-plate type, a plurality of systems of the lens units 5121 are also provided corresponding to the imaging elements.

Further, the imaging unit 5123 does not necessarily have to be provided on the camera head 5119. For example, the imaging unit 5123 may be provided immediately after an objective lens inside the lens-barrel 5117.

The driving unit 5125, which is constituted by an actuator, moves the zoom lens and the focus lens of the lens unit 5121 along an optical axis by a predetermined distance under the control of the camera head control unit 5129. Thereby, the magnification and focus of a captured image obtained by the imaging unit 5123 can be appropriately adjusted.

The communication unit 5127 is configured of a communication device for transmitting or receiving various information to or from the CCU 5153. The communication unit 5127 transmits an image signal obtained from the imaging unit 5123 to the CCU 5153 through the transmission cable 5179 as RAW data. At this time, it is preferable that the image signal be transmitted by optical communication in order to display a captured image of a surgical part with low latency. This is because the surgeon 5181 performs a surgical operation while observing the state of an affected part by the captured image during the surgical operation, and thus it is required that a moving image of a surgical part is displayed in real time as much as possible for a safer and more reliable surgical operation. In a case where optical communication is performed, the communication unit 5127 is provided with a photoelectric conversion module that converts an electrical signal into an optical signal. An image signal is converted into an optical signal by the photoelectric conversion module and is then transmitted to the CCU 5153 through the transmission cable 5179.

In addition, the communication unit 5127 receives a control signal for controlling the driving of the camera head 5119 from the CCU 5153. The control signal includes information on imaging conditions such as information indicating designation of a frame rate of a captured image, information indicating designation of an exposure value during imaging, and/or information indicating designation of magnification and focus of a captured image. The communication unit 5127 provides the received control signal to the camera head control unit 5129. Meanwhile, the control signal received from the CCU 5153 may also be transmitted by optical communication. In this case, the communication unit 5127 is provided with a photoelectric conversion module that converts an optical signal into an electrical signal, and the control signal is converted into an electrical signal by the photoelectric conversion module and is then provided to the camera head control unit 5129.

Meanwhile, the above-described imaging conditions such as a frame rate, an exposure value, magnification, and focus are automatically set by the control unit 5177 of the CCU 5153 on the basis of an acquired image signal. That is, the endoscope 5115 is equipped with a so-called auto exposure (AE) function, auto focus (AF) function, and auto white balance (AWB) function.

The camera head control unit 5129 controls the driving of the camera head 5119 on the basis of the control signal from the CCU 5153 received via the communication unit 5127. For example, the camera head control unit 5129 controls the driving of the imaging element of the imaging unit 5123 on the basis of information indicating designation of a frame rate of a captured image and/or information indicating designation of exposure during imaging. In addition, for example, the camera head control unit 5129 appropriately moves the zoom lens and the focus lens of the lens unit 5121 through the driving unit 5125 on the basis of information indicating designation of magnification and focus of a captured image. The camera head control unit 5129 may further have a function of storing information for identifying the lens-barrel 5117 and the camera head 5119.

Meanwhile, components such as the lens unit 5121 and the imaging unit 5123 are disposed within a sealed structure with high airtightness and waterproofness, and thus the camera head 5119 can be made resistant to autoclave sterilization.

Next, a functional configuration of the CCU 5153 will be described. The communication unit 5173 is configured of a communication device for transmitting and receiving various pieces of information to and from the camera head 5119. The communication unit 5173 receives an image signal transmitted from the camera head 5119 via the transmission cable 5179. At this time, as described above, the image signal can be suitably transmitted through optical communication. In this case, for the optical communication, the communication unit 5173 is provided with a photoelectric conversion module that converts an optical signal into an electric signal. The communication unit 5173 provides the image signal converted into the electric signal to the image processing unit 5175.

Further, the communication unit 5173 transmits a control signal for controlling the driving of the camera head 5119 to the camera head 5119. The control signal may also be transmitted by optical communication.

The image processing unit 5175 performs various image processing on the image signal which is the RAW data transmitted from the camera head 5119. Examples of the image processing include various known signal processing such as development processing, high image quality processing (band enhancement processing, super-resolution processing, noise reduction (NR) processing, and/or camera shake correction processing), and/or enlargement processing (electronic zoom processing). In addition, the image processing unit 5175 performs detection processing on an image signal for performing AE, AF, and AWB.

The image processing unit 5175 is constituted by a processor such as a CPU or a GPU, and the above-described image processing and detection processing can be performed by the processor operating in accordance with a predetermined program. Meanwhile, in a case where the image processing unit 5175 is constituted by a plurality of GPUs, the image processing unit 5175 appropriately divides information related to an image signal and performs image processing in parallel by the plurality of GPUs.

The control unit 5177 performs various control related to imaging of a surgical part and display of a captured image thereof which are performed by the endoscope 5115. For example, the control unit 5177 generates a control signal for controlling the driving of the camera head 5119. At this time, in a case where imaging conditions are input by a user, the control unit 5177 generates a control signal on the basis of the user's input. Alternatively, in a case where the endoscope 5115 is equipped with an AE function, an AF function, and an AWB function, the control unit 5177 appropriately calculates an optimal exposure value, focal distance, and white balance in accordance with results of the detection processing performed by the image processing unit 5175 to generate a control signal.

In addition, the control unit 5177 displays an image of a surgical part on the display device 5155 on the basis of an image signal having been subjected to image processing by the image processing unit 5175. At this time, the control unit 5177 recognizes various objects in a surgical part image using various image recognition techniques. For example, the control unit 5177 can recognize surgical instruments such as forceps, specific biological parts, bleeding, mist at the time of using the energy treatment tool 5135, and the like by detecting the shape, color, and the like of an edge of an object included in a surgical part image. The control unit 5177 displays various surgical operation supporting information so as to be superimposed on an image of a surgical part by using recognition results thereof at the time of displaying the image of the surgical part on the display device 5155. The surgical operation supporting information is displayed to be superimposed and is presented to the surgeon 5181, and thus it is possible to proceed with a surgical operation more safely and reliably.

The transmission cable 5179 connecting the camera head 5119 and the CCU 5153 to each other is an electric signal cable that supports electric signal communication, an optical fiber that supports optical communication, or a composite cable thereof.

Here, in the example shown in the drawing, communication is performed in a wired manner using the transmission cable 5179, but communication between the camera head 5119 and the CCU 5153 may be performed in a wireless manner. In a case where communication therebetween is performed in a wireless manner, the transmission cable 5179 does not need to be built in a surgical operating room, and thus a situation where the movement of a medical staff in the surgical operating room is hindered by the transmission cable 5179 can be solved.

The example of the operating room system 5100 to which the technology according to the present disclosure may be applied has been described above. Also, although the case in which a medical system to which the operating room system 5100 is applied is the endoscopic surgery system 5113 has been described here as an example, the configuration of the operating room system 5100 is not limited to such an example. For example, the operating room system 5100 may be applied to a flexible endoscopic system for examination or a microsurgery system instead of the endoscopic surgery system 5113.

The technology according to the present disclosure can be suitably applied to imaging of the hands of a surgeon using the ceiling camera 5187, imaging of a state of the entire operating room using the operating room camera 5189, imaging of a surgical side the using the endoscope 5115, and the like among the above-described configurations. Specifically, the technology according to the present disclosure can be applied by a control unit (e.g., CCU 5153) adjusting irises (optical diaphragms) provided in the ceiling camera 5187, the operating room camera 5189, and the endoscope 5115 and a gain of an imaging device on the basis of an operation input of a user from a controller (e.g., input device 5161). By applying the technology according to the present disclosure to such imaging, it is possible to promote mitigation of a discomfort of a user during brightness adjustment switching and curbing of deterioration in operability with respect to brightness adjustment while promoting curbing of resolution decrease due to execution of only optical brightness adjustment with respect to capturing of images with respect to surgery. Particularly, when the technology according to the present disclosure is applied to imaging using the endoscope 5115, abrupt change in brightness with respect to a captured image of a surgical site is curbed, and thus artifacts of the surgical site can be curbed to improve stability of surgery.

Meanwhile, the effects described in the present specification are merely exemplary and other effects may be obtained.

6. Present Technology

Meanwhile, the present technology can employ the following configurations.

(1)
A signal processing device including; a switching unit that performs, in response to change in an indication value indicating the brightness of a captured image obtained by an imaging device, switching between optical brightness adjustment that is brightness adjustment according to an iris and electronic brightness adjustment that is brightness adjustment according to application of a gain depending on the indication value to the captured image; and
a first delay unit that delays change in the gain with respect to change in the indication value in electronic brightness adjustment.

(2)
The signal processing device according to (1), wherein the indication value is a target value of an F value.

(3)
The signal processing device according to (1) or (2), wherein the switching unit performs the switching control on the basis of a result of comparison between the indication value and a threshold value.

(4)
The signal processing device according to (3), wherein the indication value is a target value of an F value, and
the switching unit performs the switching control such that the optical brightness adjustment is performed on a side on which the target value of the F value is large and the electronic brightness adjustment is performed on a side on which the target value of the F value is small, with respect to the threshold value.

(5)
The signal processing device according to any one of (1) to (4), wherein the first delay unit changes a gain change speed within a period in which the gain is changed in the electronic brightness adjustment.

(6)
The signal processing device according to any one of (1) to (5), wherein the first delay unit suppresses the gain change speed to a predetermined speed or less in the electronic brightness adjustment.

(7)
The signal processing device according to any one of (1) to (6), wherein the first delay unit delays the gain according to delay characteristics imitating inertia in the electronic brightness adjustment.

(8)
The signal processing device according to any one of (1) to (7), wherein the switching unit is configured to be able to switch between a switching mode in which control of switching between the optical brightness adjustment and the electronic brightness adjustment is performed in response to change in the indication value and a non-switching mode in which the switching control is not performed with respect to change in the indication value and the optical brightness adjustment is executed.

(9)
The signal processing device according to (8), wherein the switching unit performs switching between the switching mode and the non-switching mode on the basis of an operation.

(10)
The signal processing device according to (9), wherein the switching unit performs switching between the switching mode and the non-switching mode on the basis of an operation of a remote controller.

(11)
The signal processing device according to any one of (1) to (10), wherein the first delay unit is configured to be able to change delay characteristics of the gain in the electronic brightness adjustment.

(12)
The signal processing device according to (11), wherein the imaging device is a lens interchangeable type imaging device, and
the first delay unit delays change in the gain according to delay characteristics based on information acquired from a lens device mounted in the imaging device.

(13)
The imaging device according to any one of (1) to (12), including a second delay unit that delays change in the F value with respect to change in the indication value in the optical brightness adjustment.

REFERENCE SIGNS LIST

1 Imaging device
1, 1A, 1C, 1D Imaging device
2 Imaging element
3 First correction processing unit
4 Amplification unit
5 Second correction processing unit
6 Development processing unit
7, 7A, 7B, 7C, 7D Control unit
7a Switching unit
7b, 7c, 8 Filter unit
10, 10A Lens device
11 Iris driving unit
12 Storage unit
12a Filter characteristic information
20, 20D Camera control unit (CCU)
20a Control unit
30 Remote controller
30a Adjustment operator

The invention claimed is:

1. A signal processing device, comprising:
an imaging device configured to capture an image; and
a central processing unit (CPU) configured to:
control switch between a switching mode and a non-switching mode, wherein
in the switching mode, the CPU is further configured to:
perform, based on a change in an indication value indicating a brightness of the captured image, switching control between an optical brightness adjustment of the captured image and an electronic brightness adjustment of the captured image, wherein
the optical brightness adjustment of the captured image is based on a drive of an iris,
the electronic brightness adjustment of the captured image is based on application of a gain on the captured image, and
the gain is based on the indication value; and
delay, based on the change in the indication value, change in the gain in the electronic brightness adjustment,
in the non-switching mode, the CPU is further configured to execute the optical brightness adjustment, and in the non-switching mode, the switching control is not performed based on the change in the indication value.

2. The signal processing device according to claim 1, wherein the indication value is a target value of an F value.

3. The signal processing device according to claim 1, wherein the CPU is further configured to:
compare the indication value with a threshold value; and
perform, based on the comparison, the switching control between the optical brightness adjustment and the electronic brightness adjustment.

4. The signal processing device according to claim 3, wherein
the indication value is a target value of an F value, and the CPU is further configured to:
perform the optical brightness adjustment in a region where the target value of the F value is larger than the threshold value; and
perform the electronic brightness adjustment in a region where the target value of the F value is smaller than the threshold value.

5. The signal processing device according to claim 1, wherein
the CPU is further configured to change a gain change speed within a period in which the gain is changed in the electronic brightness adjustment.

6. The signal processing device according to claim 1, wherein the CPU is further configured to suppress a gain change speed to one of equal to or less than a specific speed in the electronic brightness adjustment.

7. The signal processing device according to claim 1, wherein
the CPU is further configured to delay the gain based on according to delay characteristics of the gain, and
the delay characteristics imitates inertia in the electronic brightness adjustment.

8. The signal processing device according to claim 1, wherein the CPU is further configured to control the switch between the switching mode and the non-switching mode based on an operation.

9. The signal processing device according to claim 8, wherein the CPU is further configured to control the switch between the switching mode and the non-switching mode based on the operation of a remote controller.

10. The signal processing device according to claim 1, wherein the CPU is further configured to change delay characteristics of the gain in the electronic brightness adjustment.

11. The signal processing device according to claim 10, further comprising a lens device mountable on the imaging device, wherein
the imaging device is a lens interchangeable type imaging device,
the CPU is further configured to:
acquire information from the lens device, and
delay change in the gain based on the delay characteristics of the gain, and
the delay characteristics is based on the information acquired from the lens device mounted in the imaging device.

12. The imaging device according to claim 2, wherein
the CPU is further configured to delay change in the F value in the optical brightness adjustment, and
the change in the F value is based on the change in the indication value.

13. An imaging device, comprising:
an imaging element configured to receive incident light through an iris to acquire a captured image; and
a central processing unit (CPU) configured to:
control switch between a switching mode and a non-switching mode, wherein
in the switching mode, the CPU is further configured to:
perform, based on a change in an indication value indicating a brightness of the captured image, switching control between an optical brightness adjustment of the captured image and an electronic brightness adjustment of the captured image, wherein
the optical brightness adjustment of the captured image is based on a drive of the iris,
the electronic brightness adjustment of the captured image is based on application of a gain on the captured image, and
the gain is based depending on the indication value to the captured image; and
delay, based on the change in the indication value, change in the gain in the electronic brightness adjustment,
in the non-switching mode, the CPU is further configured to execute the optical brightness adjustment, and
in the non-switching mode, the switching control is not performed based on the change in the indication value.

14. A signal processing method, comprising:
capturing, by an imaging device, an image;
controlling, by a central processing unit (CPU), switching between a switching mode and a non-switching mode, wherein
in the switching mode,
performing, by the CPU, switching control between an optical brightness adjustment of the captured image and an electronic brightness adjustment of the captured image, wherein
the switching control is performed based on a change in an indication value indicating a brightness of the captured image,
the optical brightness adjustment of the captured image is based on a drive of an iris,
the electronic brightness adjustment of the captured image is based on application of a gain on the captured image, and
the gain is based on the indication value; and
delaying, by the CPU, change in the gain in the electronic brightness adjustment, based on the change in the indication value; and
in the non-switching mode, executing, by the CPU, the optical brightness adjustment, wherein
in the non-switching mode, the switching control is not performed based on the change in the indication value.

* * * * *